US012220531B2

(12) United States Patent
Nilforushan

(10) Patent No.: US 12,220,531 B2
(45) Date of Patent: Feb. 11, 2025

(54) AIRWAY DEVICES AND METHODS OF USE THEREOF

(71) Applicant: Vahid Nilforushan, West Vancouver (CA)

(72) Inventor: Vahid Nilforushan, West Vancouver (CA)

(*) Notice: Subject to any disclaimer, the term of this patent is extended or adjusted under 35 U.S.C. 154(b) by 0 days.

(21) Appl. No.: 18/596,861

(22) Filed: Mar. 6, 2024

(65) Prior Publication Data

US 2024/0207557 A1 Jun. 27, 2024

Related U.S. Application Data

(63) Continuation of application No. PCT/CA2023/051404, filed on Oct. 23, 2023.

(60) Provisional application No. 63/543,019, filed on Oct. 6, 2023, provisional application No. 63/528,644, filed on Jul. 25, 2023, provisional application No. 63/526,460, filed on Jul. 13, 2023, provisional
(Continued)

(51) Int. Cl.
*A61M 16/04* (2006.01)
*A61M 16/00* (2006.01)

(52) U.S. Cl.
CPC .... *A61M 16/0488* (2013.01); *A61M 16/0003* (2014.02); *A61M 2210/065* (2013.01); *A61M 2210/0656* (2013.01)

(58) Field of Classification Search
CPC ............ A61M 16/0488; A61M 16/049; A61M 16/0495; A61M 16/0497; A61B 1/267
See application file for complete search history.

(56) References Cited

U.S. PATENT DOCUMENTS 2,474,857 A * 7/1949 Newman ................. A61B 17/02
600/206
3,153,267 A * 10/1964 Rowland, Jr. ............ A61B 1/24
24/339
(Continued)

FOREIGN PATENT DOCUMENTS

CN 107049224 A * 8/2017 ......... A61B 1/00064
EP 0944346 B1 10/2001
(Continued)

OTHER PUBLICATIONS

Teleflex LMA Fastrach instruction sheet.

*Primary Examiner* — Kathryn E Ditmer
(74) *Attorney, Agent, or Firm* — Oyen Wiggs Green & Mutala LLP

(57) ABSTRACT

Airway devices and uses of such airway devices are disclosed. The airway device comprises an elongated blade having first and second longitudinal edges and proximal and distal lateral edges. The blade has a proximal region that is proximate to the proximal lateral edge, and a distal region that is proximate to the distal lateral edge. The blade may have a substantially flat configuration. In some embodiments, a pair of side components is arranged laterally spaced-apart in mirror image symmetry with respect to a central longitudinal axis of the blade. Each of the side components is arranged to project outwardly from a first face of the elongated blade at the distal region thereof. A distal plate region may be defined by a space separating the pair of side components, dimensioned for an airway or ventilation device such as an ETT to pass therethrough towards a distal tip of the blade.

28 Claims, 29 Drawing Sheets

Related U.S. Application Data application No. 63/449,320, filed on Mar. 2, 2023, provisional application No. 63/418,567, filed on Oct. 23, 2022.

(56) References Cited

U.S. PATENT DOCUMENTS

| | | | |
|---|---|---|---|
| 3,306,298 A * | 2/1967 | Raimo | A61M 16/0488 128/207.14 |
| 3,749,088 A * | 7/1973 | Kohlmann | A61B 17/0293 74/540 |
| 3,756,244 A * | 9/1973 | Kinnear | A61M 16/0488 128/207.14 |
| 3,771,514 A * | 11/1973 | Huffman | A61B 1/0661 359/837 |
| 3,774,616 A * | 11/1973 | White | A61M 16/0497 128/200.26 |
| 4,612,927 A * | 9/1986 | Kruger | A61M 16/0488 128/200.26 |
| 4,793,327 A | 12/1988 | Frankel | |
| 5,042,469 A | 8/1991 | Augustine | |
| 5,303,697 A | 4/1994 | Brain | |
| 5,323,771 A | 6/1994 | Fisher et al. | |
| 5,513,627 A | 5/1996 | Flam | |
| 5,720,275 A * | 2/1998 | Patil | A61M 16/0418 128/207.14 |
| 5,743,254 A | 4/1998 | Parker | |
| 5,896,858 A | 4/1999 | Brain | |
| 5,937,859 A | 8/1999 | Augustine et al. | |
| 6,045,499 A * | 4/2000 | Pitesky | A61B 13/00 600/240 |
| 6,053,166 A * | 4/2000 | Gomez | A61M 16/0493 128/207.14 |
| 6,079,409 A | 6/2000 | Brain | |
| 6,257,238 B1 * | 7/2001 | Meah | A61B 1/24 128/200.26 |
| 6,672,305 B2 | 1/2004 | Parker | |
| 6,679,257 B1 * | 1/2004 | Robertson | A61M 16/0493 128/204.18 |
| 6,718,970 B2 * | 4/2004 | Sniadach | A61M 16/0409 128/207.14 |
| 7,128,071 B2 | 10/2006 | Brain | |
| RE39,508 E | 3/2007 | Parker | |
| 8,522,789 B2 | 9/2013 | Miller et al. | |
| 8,931,477 B2 * | 1/2015 | Ogilvie | A61M 16/0493 128/207.14 |
| 9,475,223 B2 | 10/2016 | Nasir | |
| 9,956,367 B1 | 5/2018 | Sun | |
| 10,542,873 B2 | 1/2020 | Uesugi et al. | |
| 2004/0060564 A1 | 4/2004 | Brain | |
| 2008/0276932 A1 * | 11/2008 | Bassoul | A61M 16/0463 128/200.26 |
| 2009/0101140 A1 * | 4/2009 | Miller | A61M 16/04 128/200.26 |
| 2010/0041955 A1 * | 2/2010 | Grey | A61L 29/041 600/212 |
| 2010/0298644 A1 * | 11/2010 | Kleene | A61B 1/2676 128/207.14 |
| 2011/0120474 A1 * | 5/2011 | Daugherty | A61M 16/0495 128/207.17 |
| 2011/0137127 A1 * | 6/2011 | Schwartz | A61B 1/05 600/188 |
| 2011/0178372 A1 * | 7/2011 | Pacey | A61B 1/00142 600/188 |
| 2013/0098366 A1 * | 4/2013 | Chen | A61M 16/04 128/207.15 |
| 2013/0211263 A1 | 8/2013 | Boedeker | |
| 2013/0319406 A1 * | 12/2013 | Borrye | A61M 16/0488 128/200.26 |
| 2014/0238390 A1 * | 8/2014 | Wei | A61B 1/267 128/200.26 |
| 2015/0141942 A1 * | 5/2015 | Garrett | A61M 1/84 604/319 |
| 2016/0166791 A1 * | 6/2016 | Kleene | A61M 16/0488 600/188 |
| 2017/0224200 A1 * | 8/2017 | Uesugi | A61B 1/2676 |
| 2019/0054266 A1 * | 2/2019 | Sun | A61M 16/0447 |
| 2020/0114105 A1 * | 4/2020 | Molnar | A61B 1/053 |
| 2020/0376219 A1 | 12/2020 | Elton | |
| 2021/0162154 A1 * | 6/2021 | Sun | A61M 16/0418 |
| 2021/0308403 A1 * | 10/2021 | Gao | A61B 1/0014 |
| 2023/0100909 A1 * | 3/2023 | Peck | A61B 1/0057 128/200.26 |

FOREIGN PATENT DOCUMENTS

| | | | | |
|---|---|---|---|---|
| GB | 2546167 B | | 2/2018 | |
| KR | 101789171 B1 * | | 10/2017 | |
| WO | WO-2007048884 A1 * | | 5/2007 | ........ A61M 16/0488 |
| WO | WO-2008006968 A3 * | | 3/2008 | ............ A61M 16/04 |
| WO | 2012170681 A1 | | 12/2012 | |

* cited by examiner

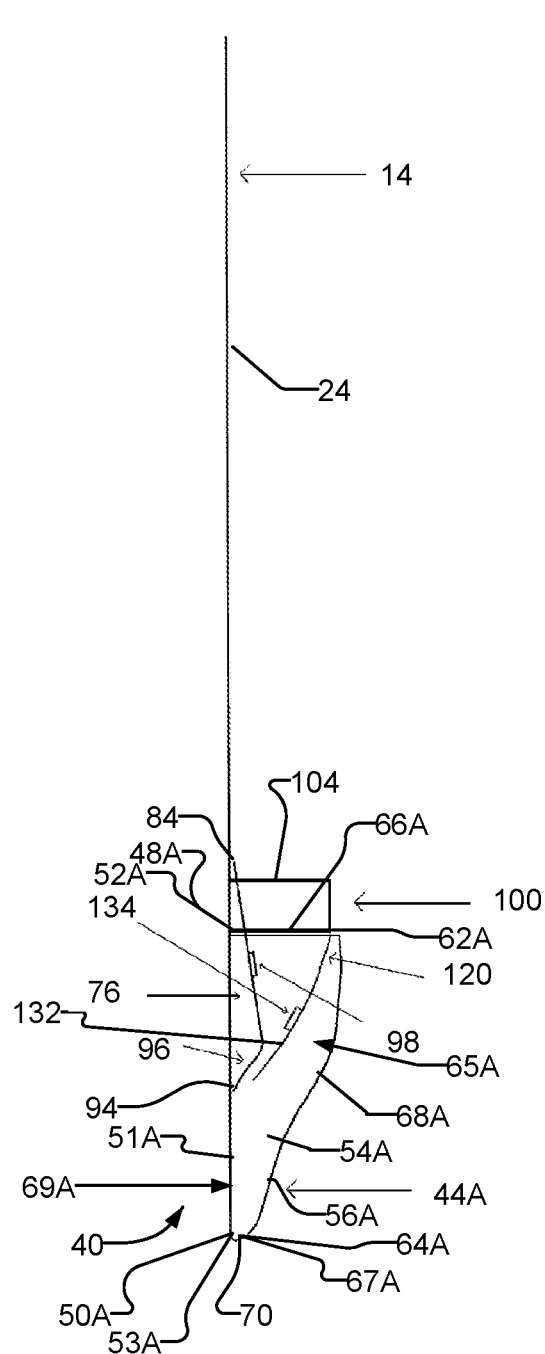
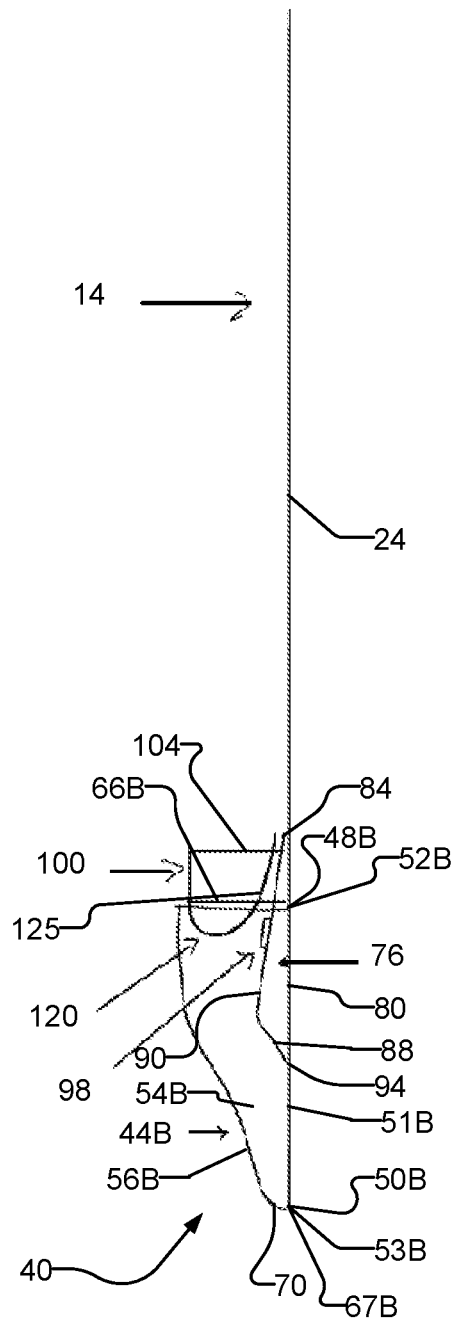
FIG. 2A
FIG. 2B

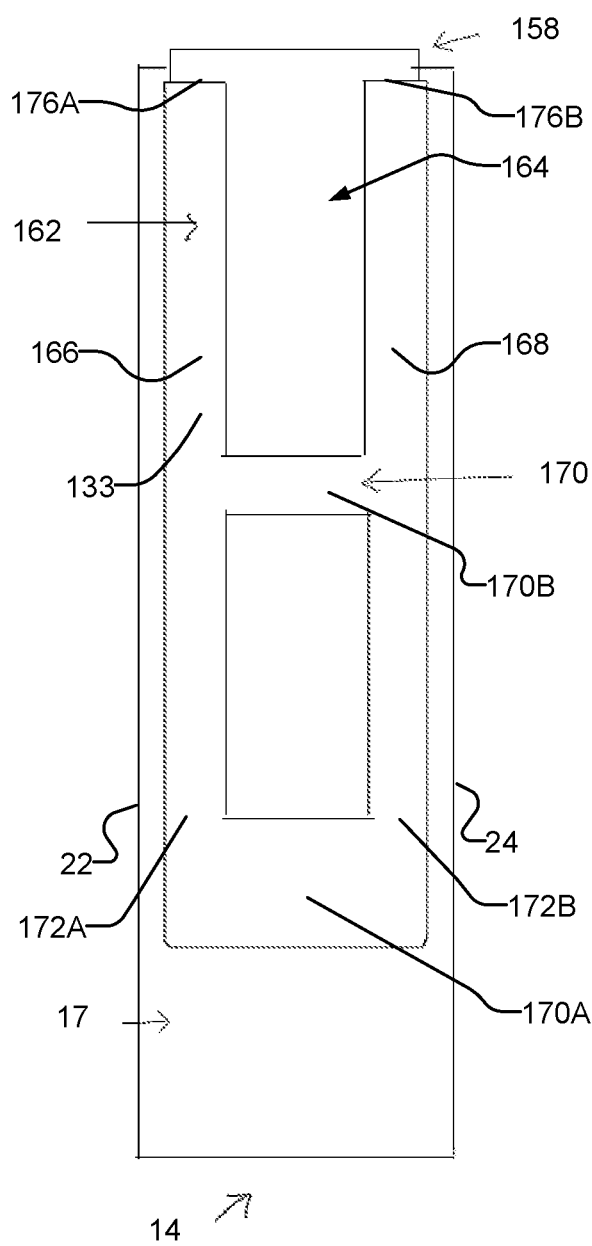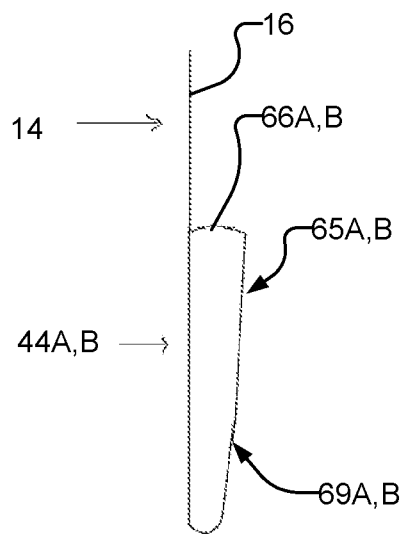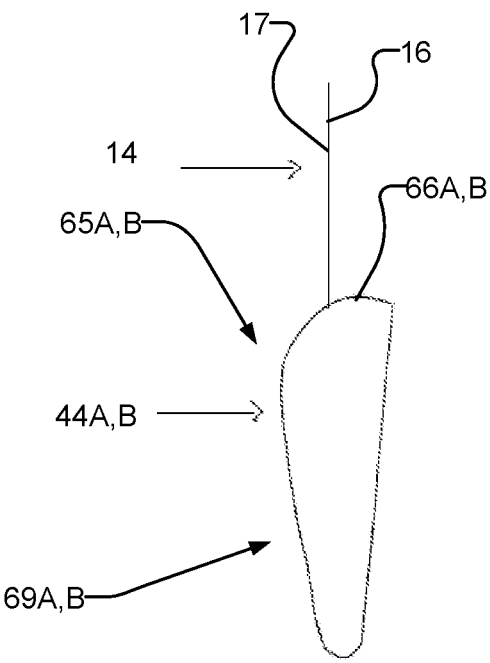
FIG. 9
FIG. 10A
FIG. 10B

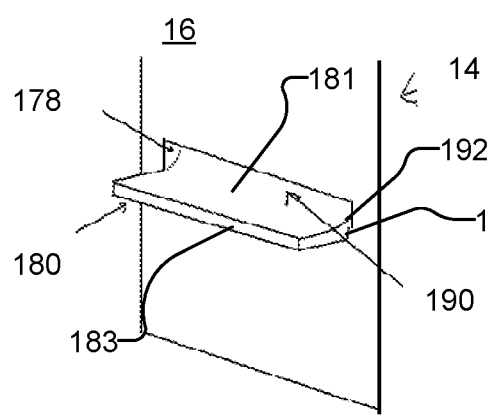
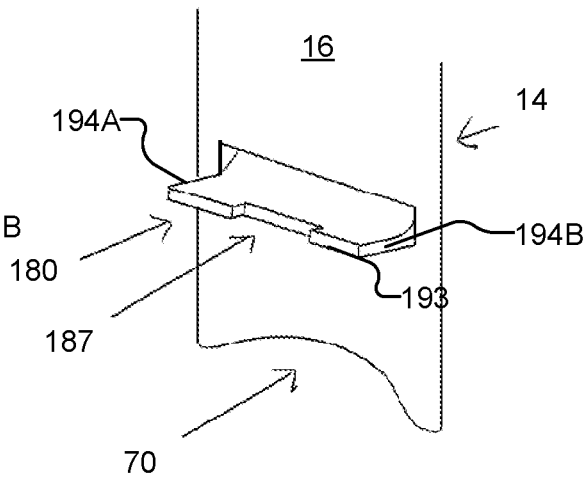
FIG. 17A  FIG. 17B
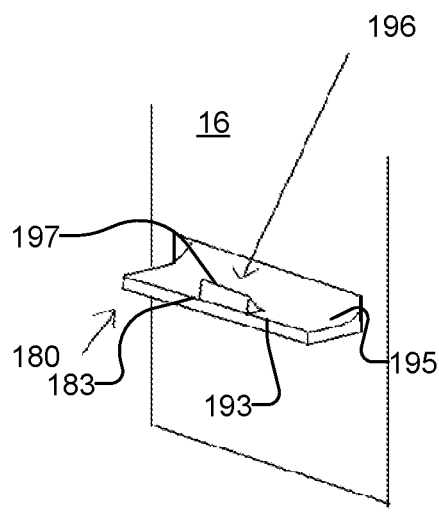
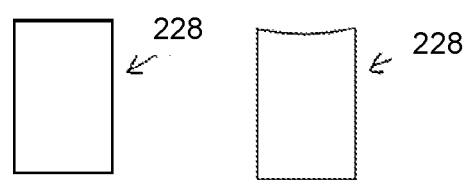
FIG. 18A  FIG. 18B
FIG. 17C
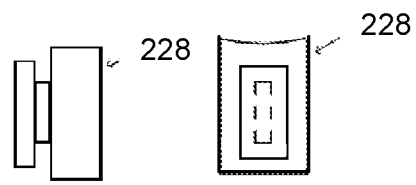
FIG. 19A  FIG. 19B

AIRWAY DEVICES AND METHODS OF USE THEREOF

CROSS-REFERENCE TO RELATED APPLICATIONS

This application is a continuation of PCT application No. PCT/CA2023/051404 filed 23 Oct. 2023. PCT application No. PCT/CA2023/051404 claims priority from U.S. application No. U.S. 63/418,567 filed 23 Oct. 2022 and entitled BLIND ENDOTRACHEAL INTUBATION DEVICE, U.S. application No. 63/449,320 filed 2 Mar. 2023 and entitled ENDOTRACHEAL INTUBATION DEVICE, U.S. application No. 63/526,460 filed 13 Jul. 2023 and entitled ENDOTRACHEAL INTUBATION DEVICE, U.S. application No. 63/528,644 filed 25 Jul. 2023 and entitled ENDOTRACHEAL INTUBATION DEVICE, and U.S. application No. 63/543,019 filed 6 Oct. 2023 and entitled ENDOTRACHEAL INTUBATION DEVICE, all of which are hereby incorporated herein by reference for all purposes. For purposes of the United States of America, this application claims the benefit under 35 U.S.C. § 119 of U.S. application No. U.S. 63/418,567 filed 23 Oct. 2022 and entitled BLIND ENDOTRACHEAL INTUBATION DEVICE, U.S. application No. 63/449,320 filed 2 Mar. 2023 and entitled ENDOTRACHEAL INTUBATION DEVICE, U.S. application No. 63/526,460 filed 13 Jul. 2023 and entitled ENDOTRACHEAL INTUBATION DEVICE, U.S. application No. 63/528,644 filed 25 Jul. 2023 and entitled ENDOTRACHEAL INTUBATION DEVICE, and U.S. application No. 63/543,019 filed 6 Oct. 2023 and entitled ENDOTRACHEAL INTUBATION DEVICE.

FIELD OF THE INVENTION

This invention relates to airway devices, in particular those that may be used in a plurality of applications such as to open and maintain an airway of a subject and/or to assist ventilation.

BACKGROUND

Visualizing the larynx by laryngoscopy is currently the standard of clinical practice for endotracheal intubation. However, visualizing laryngeal structures and intubation by this method is not always possible because of the unique makeup of the particular subject to be operated on, including for example, limitations of jaw or neck movement, swelling of the soft tissues of the mouth, throat, and larynx, and/or an unusual size or anatomy of the airway, etc. Using conventional techniques of visualized or blind intubation in expected or unexpected cases of difficult intubation requires for other rescue intubation devices and more reliable methods of handling such cases.

An important consideration in airway management is that cases of difficult intubation and/or ventilation sometimes happen when they are not expected. In these critical and life-threatening situations, healthcare practitioners are usually less prepared.

Endotracheal intubation by visualizing the larynx in out-of-hospital situations such as cardiopulmonary resuscitations or trauma where patients need to be intubated within seconds also has its challenges. Intubation by direct or video laryngoscopy requires extensive training and practice and this significantly lowers the number of healthcare workers and the general public who can intubate patients in such emergency situations. Moreover, the presence of blood, vomitus, regurgitated food or copious secretions that may be seen in the oropharyngeal cavity in those situations and the unavailability or ineffectiveness of the suctioning devices or delay in accessing them impede visualizing the larynx. Other issues that may make visualizing the larynx challenging when video laryngoscopes are used in these situations include direct solar irradiation on the screen and fogging of the lens. In cases of trauma, the limited head, neck and jaw movement and/or the need for stabilizing the neck during intubation make intubation even more challenging. Also, in these situations, other means of managing difficult airways may not be available. Since direct or video laryngoscopes consist of multiple components and require a power source to operate, device failure may also happen and this can also lead to failure in visualizing the larynx. Therefore, there is a need for intubation devices that are simple, easy to use, and do not need extensive training, do not rely on visualizing the larynx, and can be used in those with limited head, neck and jaw movement. If such devices are available, bystanders with no to minimal training would be able to intubate patients in critical situations where the seconds count, and this can save many lives.

In some situations, video laryngoscopy provides a clear view of vocal cords and laryngopharynx, but passing an endotracheal tube (ETT) through the vocal cords is challenging or impossible.

Another issue that occasionally happens is the displacement of the ETT during operations (especially in unusual positions) or in difficult airway patients in ICUs. These situations can be life-threatening and while reintubating patients immediately is critical it might not be possible. The materials used in manufacturing direct or video laryngoscopes are rigid, and this may cause dental injuries especially in cases of difficult intubation. Since the blades of direct or video laryngoscopes are placed in the anterior aspect of the oropharyngeal cavity, the laryngeal view that they provide is limited especially in cases of difficult intubation. If there are visualizing devices that are placed in the posterior aspect of the oropharyngeal cavity, a wider and better field of view of these structures can be provided which can facilitate intubation.

Some cases of difficult intubation are managed by attempts at visualizing the larynx while the patients are awake or lightly sedated and locally anesthetized, and this can be unpleasant for patients. With improvement in endotracheal intubation techniques, some of these patients can undergo general anesthesia before any attempts at intubation are made.

The need for other and more reliable methods of blind endotracheal intubation became more apparent after the COVID-19 pandemic. Since visualizing the larynx and vocal cords by direct laryngoscopy, which is the usual and cheap method of intubation, requires the proximity of the healthcare provider to the patient's nose, mouth and respiratory secretions this poses the risk of transmission of serious respiratory disease to healthcare providers. Because of this, in most countries, direct laryngoscopy was replaced by video laryngoscopy and this in turn led to the use of disposable video laryngoscope blades in some countries which was associated with a significant increase in healthcare costs.

In some cases of difficult intubation, the ETT needs to be removed or exchanged after certain measures are in place.

Many currently available devices that are used for the management of difficult airway are bulky and cannot be passed easily through the mouth, nose or oral cavity in the cases of difficult intubation or ventilation.

Supraglottic airway devices such as laryngeal mask airways (LMAs) and i-Gel™ which are currently commonly used for supraglottic ventilation have been used for blind or fiberoptic guided intubation as well. However, their use requires training and expertise and they are associated with risks of pulmonary aspiration when they are used for supraglottic ventilation in situations where the patients need to be intubated such as in many out-of-hospital scenarios. Blind intubation by these devices is not always successful or can be associated with tissue injury or the downfolding of the epiglottis which can lead to epiglottis injury or swelling and airway obstruction after extubation if not diagnosed early. These issues are seen with other supraglottic airway devices such as the laryngeal tube and esophageal-tracheal combitube as well. There is thus a need for more reliable devices that can be used for blind intubation with no to minimal training, especially in out-of-hospital intubations.

The size of the ETTs that can be passed through current supraglottic devices for blind endotracheal intubation is limited and the passage of the ETT through them is not usually easy because of the high friction and resistance with the internal wall of the LMAs.

Intubating LMA (Fastrach™), which is a special type of laryngeal mask airway designed for blind or fiberoptic guided endotracheal intubation in cases of difficult airway has many drawbacks. It includes a rigid airway tube which may not be easy to pass through the oropharyngeal cavity and which can lead to airway edema. Its use also requires training. The Fastrach™ can also only be used with a special ETT and not with conventional ETTs. There is also a need to use a lubricant for the passage of the special ETT through the Fastrach™ lumen. It comes in three sizes only and cannot be used in those under 30 kg as well. The removal of the Fastrach™ after intubation also requires the use of a stabilizer rod which makes the process of intubation complex, which requires further training, and slow and may lead to accidental extubation during the removal of the Fastrach™. Downfolding of the epiglottis may occur by the tip of the Fastrach™ during the advancement of the Fastrach™ or when the ETT is passed behind the epiglottis elevating bar. Since the downfolding of the epiglottis does not usually interfere with the process of intubation, it may not be recognized and this can lead to epiglottis injury and swelling. The need for inflation of the cuff of the Fastrach™ and checking its integrity before insertion adds two more steps to the process of intubation and this along with other steps makes the process of intubation by Fastrach™ slow.

The process of manufacturing most currently available devices used for visualized or blind endotracheal intubation is complex and the associated costs are high. Simplifying this process can lower the healthcare costs. Additionally, the cost of most rescue intubation devices and video laryngoscopes is high and this makes the availability of these devices challenging in low-resource settings. Reusing or recycling some of the devices used for visualized or blind endotracheal intubation is not possible.

There is thus a desire for improved airway devices that may be used for visualized or blind endotracheal intubation that are easy and/or inexpensive to manufacture, and easy and rapid to use particularly when unexpected resuscitations are necessary, while allowing for reliably accurate placement of airway or respiratory devices such as an endotracheal tube (ETT) at the desired location within the oropharyngeal cavity or laryngopharyngeal cavity of a subject.

SUMMARY

An aspect of the invention pertains to an airway device. The airway device comprises an elongated blade. The elongated blade comprises first and second longitudinal edges and proximal and distal lateral edges. Each of the proximal and distal lateral edges connect the first to the second longitudinal edges at opposing sides of the blade. The elongated blade has a proximal region that is proximate to the proximal lateral edge, and a distal region that is proximate to the distal lateral edge. The elongated blade may have a substantially flat configuration. In some embodiments, a pair of side components is arranged laterally spaced-apart in mirror image symmetry with respect to a central longitudinal axis of the elongated blade. Each of the side components is arranged to project outwardly from a first face of the elongated blade at the distal region thereof. A distal plate region may be defined by a space separating the pair of side components, dimensioned for an airway or ventilation device such as but not limited to an ETT to pass therethrough towards a distal tip of the blade.

An aspect of the invention pertains to the use of such airway device. In some embodiments, the airway device may be used for blind or visualized endotracheal intubation by orienting an endotracheal tube on the first face of the blade and passing the endotracheal tube through the distal plate region thereof. In other embodiments, the airway device may be used for supraglottic ventilation by inserting the airway device into a pharynx of a subject.

Further aspects of the invention and features of specific embodiments of the invention are described below.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIG. 2A is a side elevation view of an airway device according to another embodiment of the invention.

FIG. 2B is a side elevation view of the FIG. 2A embodiment showing the distal part of the epiglottis elevating bar rolled within the distal conduit.

FIG. 9 is a back elevation view of an airway device according to an embodiment of the invention.

FIG. 10A is a top elevation view of a side component according to an embodiment of the invention.

FIG. 10B is a top elevation view of a side component according to another embodiment of the invention.

FIG. 17A is a close up, perspective view, of a base guiding plate according to an example embodiment of the invention.

FIG. 17B is a close up, perspective view, of a base guiding plate according to another example embodiment of the invention.

FIG. 17C is a close up, perspective view, of a base guiding plate according to a further example embodiment of the invention.

FIG. 18A is a top view of a knob according to an example embodiment of the invention.

FIG. 18B is a top view of a knob according to another example embodiment of the invention.

FIG. 19A is a side elevation view of a knob according to another example embodiment of the invention.

FIG. 19B is front elevation view of the FIG. 19A knob according to an example embodiment of the invention.

DETAILED DESCRIPTION

Figure 1:
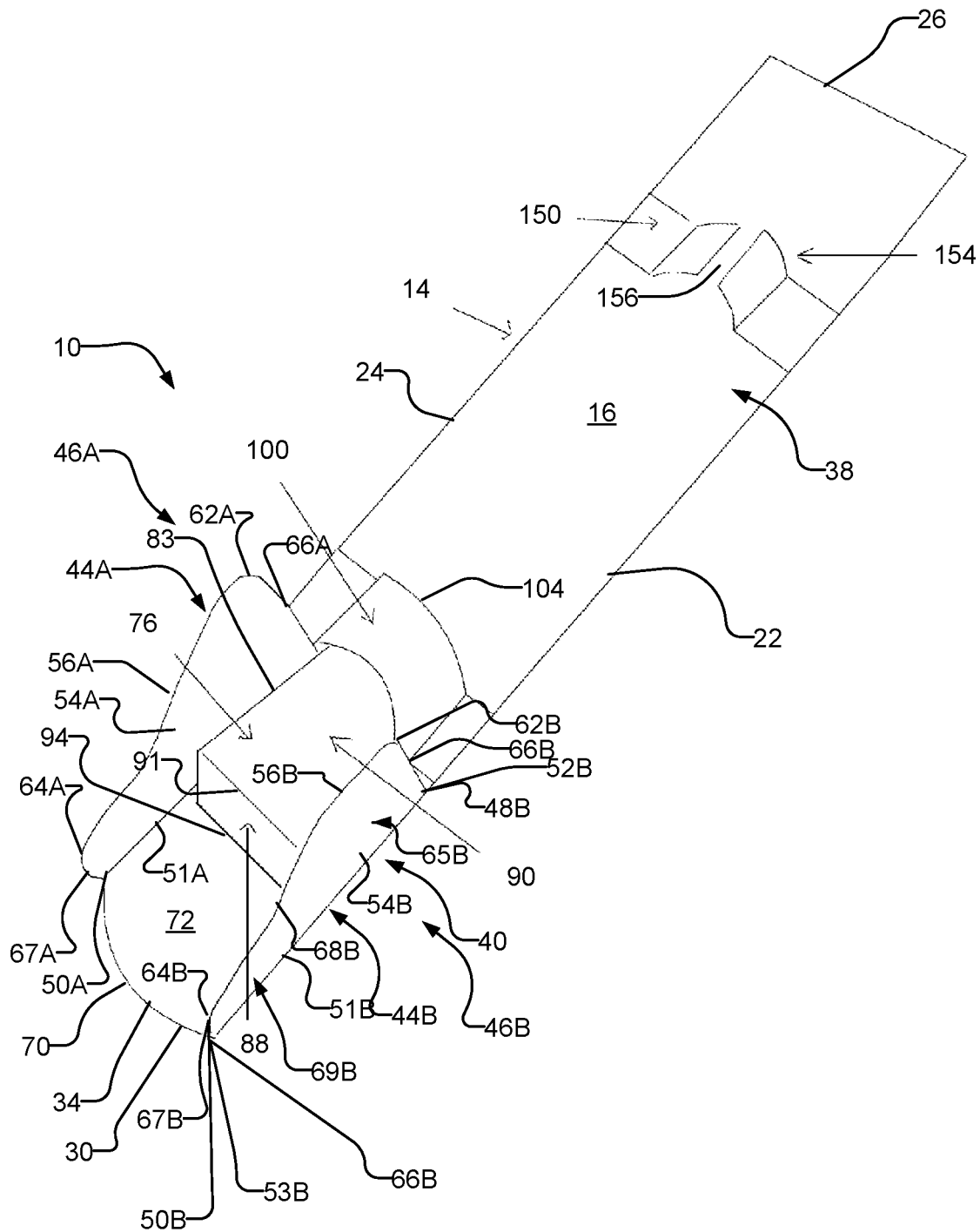
FIG. 1 is a front perspective view of an airway device according to another embodiment of the invention.

The apparatus of the present invention pertains to an airway device. The airway device may be applied in a plurality of applications. One non-limiting example application of such airway device is in blind or visualized endotracheal intubation, adapted for use with an endotracheal tube (ETT) to provide correct placement of the ETT in a trachea of a subject accurately and reliably. The airway device may also be used for supraglottic ventilation in which the device is inserted into the pharynx to allow ventilation. The airway device may also broadly be used for opening and/or maintaining an airway of a subject. The airway device may also be used to facilitate passage of a tracheal tube introducer, fiberoptic bronchoscope or a laryngoscope into the subject. It can be used for the exchange of the ETT or the passage of a suction line beside the ETT as well.

Referring to FIGS. 1-11, the airway device 10 of the invention comprises a blade 14. The blade 14 may have a first longitudinal edge 22, an opposing second longitudinal edge 24, a proximal lateral edge 26, and an opposing distal lateral edge 30. The blade 14 comprises a proximal region 38 proximate to the proximal lateral edge 26 and a distal region 40 proximate to the distal lateral edge 30. The first and second longitudinal edges 22, 24 may be arranged parallel to one another, along a longitudinal axis of the blade 14. The first and second lateral edges 26, 30 may be arranged parallel to one another, along a lateral axis of the blade 14. The first and second lateral edges 26, 30 may each connect the first longitudinal edge 22 to the second longitudinal edge 24 at opposite edges of the blade 14. In some embodiments, the blade 14 is substantially flat, with a height of the blade 14 being less than a width thereof. In some example embodiments, blade 14 comprises an elongated body, with the length of the first and second longitudinal edges 22, 24 being greater than the length of the first and second lateral edges 26, 30, i.e., the length of the blade 14 being greater than a width thereof. The blade 14 is dimensioned for insertion into and through a mouth of a subject for positioning at a desired location within the oropharyngeal cavity. In embodiments in which the device 10 is used with an ETT, the longitudinal length of the blade 14 may be adjusted depending on the longitudinal length of an ETT that a user desires to use. The longitudinal length of the blade 14 may be longer than the ETT, or shorter than the ETT. In some embodiments, the blade 14 comprises a longitudinal length that is sufficient to support the insertion of the ETT through the mouth of the subject, and into the oropharyngeal cavity. It would be apparent to the skilled person that any other suitable airway and/or respiratory device in addition to an ETT may be used with the device 10. For purposes of simplicity, an ETT would be used as an example of how such airway and/or respiratory device may be used with the present device 10.

In some embodiments, one or both of the proximal lateral edge 26 and distal lateral edge 30 are arranged substantially orthogonal to the first and second longitudinal edges 22, 24, such that the lateral edge extends from the first longitudinal edge 22 along a substantially straight region to the second longitudinal edge 24. In some embodiments, one or both of the proximal lateral edge 26 and distal lateral edge 30 extend from the first longitudinal edge 22 along a curved region 34 to the second longitudinal edge 24. In some embodiments, the curved region 34 bends downwardly to form a concave-up shape. In some embodiments, the curved region 34 bends upwardly to form a concave-down shape. In one example embodiment, the distal lateral edge 30 comprises a curved region 34 with a concave-up shape, and the proximal lateral edge 26 is substantially straight, i.e., extending substantially orthogonal to the longitudinal edges 22, 24 of the blade 14. A distal tip 70 of the blade 14 may be defined by a central point of the distal lateral edge 30 positioned at a central longitudinal axis of the blade 14. In embodiments in which the curved region 34 bends upwardly to form a concave-down shape, this configuration may facilitate passage of the distal tip 70 of the blade 14 behind the epiglottis and prevent the downfolding thereof, since the distal tip 70 of the blade 14 which is the first part of the device 10 that passes behind the epiglottis is positioned proximal to the distal lateral edges 67A,B of the side components 44A,B (as discussed in detail below). In such configuration, it is believed that the distal lateral edges 67A,B of the side components 44A,B may traverse the oropharynx before the distal tip 70 of the blade 14, thereby increasing the anteroposterior width of the oropharynx for the passage of the distal tip 70 behind the epiglottis to prevent possible undesired impingement of the distal tip 70 with the epiglottis.

The blade 14 may be made of any suitable material or combination of materials including but not limited to silicone, thermoplastic polyurethane, thermoplastic elastomers such as styrene ethylene butadiene styrene or any other types of polyurethane, polyethylene, and medically compatible polymeric materials. Different regions of the blade 14 may be formed of different materials. In such embodiments, the blade 14 may have regions comprising different physical properties. For example, the proximal region 38 of the blade 14 may comprise a material which is stiffer and/or thicker compared to the distal region 40 thereof. In another example, the distal tip 70 of the blade 14 may have a thickness greater than the thickness of the other regions along the distal region 40 and/or the proximal region 38 thereof. A thicker distal tip 70 may for example act as a blocker to prevent advancement of the ETT towards the esophagus. It would be understood that an additional element may alternatively be joined to the distal tip 70 of the blade 14 to form the blocker in order to achieve similar desired functions.

In some embodiments, a pair of side components 44A,B are arranged at the distal region 40 of the blade 14. In some embodiments, the pair of side components 44A,B are positioned laterally spaced-apart on the blade 14, each proximate to a respective one of the first and second longitudinal edges 22, 24. The pair of side components 44A,B may be arranged in mirror image symmetry about a central longitudinal axis of the blade 14. In some embodiments, the pair of side components 44A,B is joined on a first face 16 of the blade 14. In some embodiments, the pair of side components 44A,B each joins one of the first and second longitudinal edges 22, 24 of the blade 14.

The side components 44A,B may serve to displace the distal region 40 of the blade 14 upwardly and/or backwardly, and/or to maintain the distal region 40 in a central aspect of the oropharyngeal cavity. Such upward and/or backward movement may assist with passing the blade 14 through the narrow space between the pharyngeal wall and the epiglottis. The side components 44A,B may also be adapted to block spaces on each side of the larynx to prevent passage of the ETT into such undesired spaces. The side components 44A,B may further be adapted to stabilize the device 10 in place after insertion and/or widening of the space between the pharyngeal wall and the epiglottis, thereby assists to prevent undesired impingement of the central components of the blade 14 (e.g., the components positioned between the side components 44A,B, e.g., the ramp 76, the epiglottis elevating bar 120, etc.) with the epiglottis. The side components 44A,B may be made of any suitable pliable material or combination of materials, including but not limited to silicone, thermoplastic polyurethane, thermoplastic elastomers such as styrene ethylene butadiene styrene, or any other types of polyurethane, polyethylene, and medically compatible polymeric materials. In some embodiments, the side components 44A,B are formed of inflatable materials, such as silicone. In such embodiments, the side components 44A,B may be inflated before or after advancement of the device 10 into the subject.

The pair of side components 44A,B each extends distally along a longitudinal axis of the blade 14 from a first end 48A,B to a second end 50A,B to form a first longitudinal side 51A,B. In some embodiments, the first end 48A,B of the first longitudinal side 51A,B is joined to a first point 52A,B on the blade 14 and extends distally to the second end 50A,B thereof. The second end 50A,B of the first longitudinal side 51A,B may be joined to a second point 53A,B on the blade 14. The second point 53A,B of the blade 14 may in some embodiments, be on the distal lateral edge 30 of the blade 14. In some embodiments, the side components 44A,B are arranged to extend from the first point 52A,B on the blade 14 distally beyond the distal lateral edge 30 of the blade 14. In such embodiments, the second point 53A,B is not joined to the first face 16 of the blade 14. In some embodiments, the second point 53A,B of the blade 14 is positioned proximal to the distal lateral edge 30 such that the side components 44A,B do not extend to the distal lateral edge 30. As used herein, the term "distal" along the longitudinal axis of the blade means in a direction towards the distal tip 70 or the distal lateral edge 30 of the blade, and the term "proximal" along the longitudinal axis of the blade means in a direction opposite the distal tip 70 of the blade, towards the proximal lateral edge 26 of the blade. In some embodiments, the side components 44A,B do not extend an entire longitudinal length of the blade 14. The side components 44A,B may for example extend about 10% to about 35% of the entire length of the blade 14.

In some embodiments, the side components 44A,B each projects outwardly from the first longitudinal side 51A,B that is joined to the blade 14 and extends along a wall 54A,B to a second longitudinal side 56A,B that is spaced-apart from the first face 16 of the blade 14. The wall 54A,B may be arranged to extend vertically upwardly in a direction away from the face 16 of the blade 14. In some embodiments, the wall 54A,B is arranged substantially orthogonal to the first face 16 of the blade 14. In some embodiments, the wall 54A,B comprises a substantially planar wall surface.

The second longitudinal side 56A,B extends distally from a first end 62A,B to a second end 64A,B thereof. The first end 62A,B may be joined to the respective first end 48A,B by a proximal lateral edge 66A,B connecting the first to the second longitudinal edge 51A,B, 56A,B. The second end 64A,B may be joined to the respective second end 50A,B by a distal lateral side 67A,B connecting the first to the second longitudinal side 51A,B, 56A,B opposite to the proximal lateral side 66A,B. In some embodiments, the length of the proximal lateral side 66A,B is longer than the length of the distal lateral side 67A,B. The second longitudinal side 56A,B may in such embodiments extend from the first end 62A,B along a ramped region 68A,B and terminate at the second end 64A,B. In such embodiments, the height of the wall 54A,B gradually decreases as the first and second longitudinal side 51A,B, 56A,B extend from the first ends 48A,B, 62A,B to the second ends 50A,B, 64A,B thereof. The lateral cross-sectional area of the body 46A,B of the side components 44A,B thus in such embodiments decreases as the first and second longitudinal side 51A,B, 56A,B extend from the first ends 48A,B, 62A,B to the second ends 50A,B, 64A,B thereof. In some embodiments, a proximal region 65A,B of the side components 44A,B, near the proximal lateral side 66A,B thereof, extend to curve outwardly away from the first face 16 and/or second face 17 of the blade 14 (see e.g., FIG. 10B). A distal region 69A,B of the side components 44A,B may in such embodiments comprise a width that is less than the proximal region 65A,B thereof. The outward curve of the proximal region 65 of the side components 44A,B may facilitate improved placement of the device 10 in the midline and in the oropharyngeal cavity.

A distal plate region 72 of the blade 14 separates the side components 44A,B. The distal plate region 72 may be the space defined between first longitudinal sides 51A,B of the side components 44A,B. In some embodiments, the distal plate region 72 terminates at the distal lateral edge 30 of the blade 14. In some embodiments, the distal lateral sides 67A,B of the pair of side components 44A,B are proximally or distally positioned from the distal lateral edge 30 along the longitudinal axis of blade 14.

In some embodiments, a ramp 76 is secured on the first face 16 of the blade 14 at the distal region 40 thereof. In embodiments in which the device 10 is used with an ETT, the ramp 76 may serve as a guide for advancing the distal tip of the ETT towards the vocal cords of a subject. The ramp 76 comprises a first ramp longitudinal side 80 arranged proximate to and spaced-apart from one of the side components 44A,B, an opposing second ramp longitudinal side 83 arranged proximate to and spaced-apart from the other one of the side components 44A,B, a proximal ramp lateral side 84, and an opposing distal ramp lateral side 88. The proximal and distal ramp lateral sides 84,88 are each arranged to join the first ramp longitudinal side 80 to the second ramp longitudinal side 83 at opposite sides of the ramp 76. An upward sloping side joins the first and second ramp longitudinal sides 80, 83 and the proximal and distal ramp lateral sides 84, 88 to form an upward sloping face 90 of the ramp 76. In some embodiments, the proximal ramp lateral side 84 has a height less than a height of the distal ramp lateral side 88, such that the lateral cross-sectional area of the ramp 76 increases as the ramp 76 extends distally towards the direction of the distal tip 70 of the blade 14 from the proximal ramp lateral side 84 to the distal ramp lateral side 88. In such embodiments, the ramp 76 comprises an upward sloping face 90 joined to the proximal ramp lateral side 84 and extending distally to the distal ramp lateral side 88 along the longitudinal axis of the blade 14. In some embodiments, the distal ramp lateral side 88 extends substantially orthogonal to the first face 16 of the blade 14. In some embodiments, the distal ramp lateral side 88 extends downwardly at an incline towards the first face 16 of the blade 14, extending distally from a corner edge 91 that joins the face 90 to the distal ramp lateral side 88, to the second edge 94 thereof that is joined to the first face 16 of the blade 14. In some embodiments, the distal ramp lateral side 88 comprises a downward sloping face 96 joined to the corner edge 91 and extending distally to the second edge 94 thereof along the longitudinal axis of the blade 14. The downward sloping face 96 that may be defined by the distal ramp lateral side 88 may facilitate advancement of the device 10 and the epiglottis elevating bar 120 (if present, which will be discussed in detail below) through the narrow space between the epiglottis and the back wall of the throat of the subject. In some embodiments, the downward sloping face 96 has a length shorter than the upward sloping face 90.

The peak of the ramp 76 may be positioned at the corner edge 91 joining the face 90 to the distal ramp lateral side 88. In some embodiments, the height of the peak of the ramp 76 (i.e., a vertical distance measured from the first face 16 of the blade 14 to the peak of the ramp 76) is dimensioned sufficiently narrowly to allow passage of the device 10 into the narrow space between the epiglottis and the back wall of the throat of the subject, as well as to provide sufficient space for the passage of the ETT behind the epiglottis elevating bar 120 (if present).

The ramp 76 may extend distally along the longitudinal axis of the blade 14 in a direction towards the distal tip 70 of the blade 14, from the proximal ramp lateral side 84 to the distal ramp lateral side 88. In some embodiments, the proximal ramp lateral side 84 is positioned proximal to the proximal lateral edge 66A,B of the side components 44A,B along the longitudinal axis of the blade 14. In some embodiments, the proximal ramp lateral side 84 is positioned to align with, or distal to the proximal lateral side 66A,B of the side components 44A,B along the longitudinal axis of the blade 14. In some embodiments, only a portion of the ramp 76 is positioned between the side components 44A,B. In other embodiments, the entire ramp 76 may be positioned between the side components 44A,B such that the proximal and distal ramp lateral sides 84,88 are positioned between the distal and proximal lateral sides 66A,B, 67A,B of the side components 44A,B.

In some embodiments, one or more guiding plates 98 are arranged to project outwardly from the face 90 of the ramp 76. The one or more guiding plates 98 may be arranged spaced-apart from one another along the lateral axis of the ramp 76. In some embodiments, the one or more guiding plates 98 each extends along a curved region. The one or more guiding plates 98 are dimensioned to provide stability or support for an ETT which is being arranged thereon, so as to maintain the ETT along a central longitudinal axis of the blade 14 and/or to prevent unwanted lateral movement of the ETT during advancement.

In some embodiments, a distal conduit 100 is arranged at the distal region 40 of the blade 14. The distal conduit 100 may be adapted to secure an ETT close to the blade 14 and/or preserve the normal curvature of the ETT for guiding a distal tip thereof towards the vocal cords of a subject as the ETT passes through the distal conduit 100. This may advantageously eliminate the possibility of backward movement of the distal tip of the ETT towards the esophagus, particularly in situations where head, neck and/or jaw movements of the subject are limited. The distal conduit 100 may additionally assist with opening the airway by increasing the anteroposterior width of the oropharynx and moving the tongue downward and forward. The distal conduit 100 may be arranged to align with, or positioned proximal to the proximal lateral sides 66A,B of the side components 44A,B along the longitudinal axis of the blade 14. In some embodiments, the distal conduit 100 comprises a channel 104 defined by an elongated bar 108 extending from the first longitudinal edge 22 to the second longitudinal edge 24, or between the first longitudinal edge 22 to the second longitudinal edge 24, of the blade 14. The elongated bar 108 may be joined to the first longitudinal edge 22 at one end 110, and to the second longitudinal edge 24 at the opposing end 112 thereof. In other embodiments, the one end 110 and the opposing end 112 of the elongated bar 108 are joined to the first face 16 of the blade 14 laterally spaced-apart from the respective first and second longitudinal edges 22, 24 of the blade 14.

The channel 104 may be dimensioned for an ETT to pass therethrough. In some embodiments, the channel 104 comprises a substantially circular cross-sectional shape; however, the channel 104 may comprise any suitable shape for facilitating the ETT to pass therethrough and towards the distal tip 70 of the blade 14. In some embodiments, the elongated bar 108 comprises a first joined region 114 extending from the one end 110 that is joined to the first longitudinal edge 22 to a first point 115. The elongated bar 108 may comprise a second joined region (not shown) extending from the opposing end 112 that is joined to the second longitudinal edge 24 to a second point. An arched region 116 projecting outwardly from the first face 16 of the blade 14 joins the first 114 and second joined regions at the first 115 and second points. The channel 104 may be defined within the arched region 116. The first 114 and second joined regions may be joined to first face 16 of the blade 14. In some embodiments, a distance between the ends 110 of the first 114 and second joined regions and the respective first 115 and second points is substantially equal to a length of the proximal lateral edge 66A,B of the side components 44A,B. In some embodiments, the arched region 116 and thereby the channel 104 defined within the arched region 116 is positioned between the side components 44A,B. In some embodiments, the arched region 116 and thereby the channel 104 defined within the arched region 116 is positioned along a central longitudinal axis of the blade 14. The arched region 116 may comprise any suitable cross-sectional shape (e.g., rectangular, square, circular, etc.), which may or may not comprise the same as the cross-sectional shape of the channel 104. In some other embodiments, the joined regions 114 need not extend to the respective first and second longitudinal edges 22, 24 of the blade 14 but are arranged laterally spaced-apart therefrom.

In some embodiments, a portion of the ramp 76 is arranged within the channel 104, joined on the first face 16 of the blade 14 under the arched region 116. In such embodiments, the proximal ramp lateral side 84 may be arranged within the channel 104, or proximal to the channel 104 along the longitudinal axis of the blade 14. In some other embodiments, a second upward sloping ramp is arranged within the channel 104, extending distally along the longitudinal axis of the blade 14. In such embodiments, the ramp 76 is arranged distal to the distal conduit 100 along the longitudinal axis of the blade 14. It would be understood that any suitable number of ramps (e.g., more than two ramps) may be arranged on the first face 16 of the blade 14, along the longitudinal axis of the blade 14. The dimensions of each ramp may be adjusted depending on the number of ramps provided, and/or positioning thereof along the blade 14, etc.

In some embodiments, an epiglottis elevating bar 120 is arranged at the distal region 40 of the blade 14, between the side components 44A,B. The epiglottis elevating bar 120 may be oriented at an upper side of the ramp 76 opposite to the first face 16 of the blade 14. The epiglottis elevating bar 120 may in some embodiments be arranged spaced-apart from the face 90 of the ramp 76. In some embodiments, epiglottis elevating bar 120 is arranged proximate to the face 90 of the ramp 76 and/or the first face 16 of the blade 14.

In some embodiments, the epiglottis elevating bar 120 comprises a first longitudinal edge 122, an opposing second longitudinal edge 124, a proximal lateral edge 126 and an opposing distal lateral edge 128. A proximal part 123 of the epiglottis elevating bar 120 is near the proximal lateral edge 126, and a distal part 125 of the epiglottis elevating bar 120 is near the distal lateral edge 128. The proximal and distal edges 126,128 each connects the first longitudinal edge 122 to the second longitudinal edge 124 at opposite sides of the epiglottis elevating bar 120. In some embodiments, the first and second longitudinal edges 122,124 of the epiglottis elevating bar 120 are each positioned adjacent to the respective wall surfaces 58A,B of the side components 44A,B. The first and second longitudinal edges 122,124 of the epiglottis elevating bar 120 may extend distally along a longitudinal axis of the side components 44A,B within the distal plate region 72, from the proximal lateral edge 126 to the distal lateral edge 128. In some embodiments, the epiglottis elevating bar 120 is arranged to extend distally from the proximal lateral edge 126 to the distal tip 70 of the blade 14, such that the distal lateral edge 128 of the epiglottis elevating bar 120 is positioned to align with the distal lateral edge 30 of the blade 14. In some embodiments, the epiglottis elevating bar 120 is arranged to extend distally from the proximal lateral edge 126 to a point 130 between the proximal and distal lateral edges 66A,B, 68A,B of the side components 44A,B. In such embodiments, the point 130 is proximal to the distal tip 70 of the blade 14. The epiglottis elevating bar 120 may however extend distally from the proximal lateral edge 126 beyond the distal tip 70 of the blade 14 such that the distal lateral edge 128 of the epiglottis elevating bar 120 is distally positioned from the distal tip 70 of the blade 14 along the longitudinal axis of the blade 14.

In some embodiments, the epiglottis elevating bar 120 is arranged to extend to cover the entire face 90 of the ramp 76 at an upper side thereof. In such embodiments, the distal lateral edge 128 of the epiglottis elevating bar 120 may be positioned distal to the distal lateral edge 88 of the ramp 76 along the longitudinal axis of the blade 14. In some embodiments, the epiglottis elevating bar 120 is arranged to cover only a portion of the ramp 76. In such embodiments, the distal lateral edge 128 of the epiglottis elevating bar 120 may be positioned proximal to the distal ramp lateral side 88 of the ramp 76 along the longitudinal axis of the blade 14.

In some embodiments, the proximal lateral edge 126 of the epiglottis elevating bar 120 is joined to the elongated bar 108 of the distal conduit 100, and extend distally therefrom to the distal lateral edge 128 thereof. In some embodiments, the proximal lateral edge 126 of the epiglottis elevating bar 120 is joined to the arched region 116 of the elongated bar 108 of the distal conduit 100. The epiglottis elevating bar 120 may alternatively be joined to any one or more of the side components 44, the ramp 76, and/or the first face 16 of the blade 14. As used herein, the term "join" means securing two or more components together by any suitable securing means with or without fastening means including but not limited to bonding by heat, adhesive, attachment means such as hinges, hooks, loops, and the like. In some embodiments, the epiglottis elevating bar 120 and the distal conduit 100 are integrally formed.

The epiglottis elevating bar 120 is adapted to be placed behind the epiglottis of a subject when the device 10 is placed in the desired position within the oropharynx.

The epiglottis elevating bar 120 may serve to elevate the epiglottis or to move the epiglottis forward by a distal part of the ETT as the ETT is advanced through the distal conduit 100 and under the epiglottis elevating bar 120 and/or to function as a guard for the epiglottis to decrease the possibility of tissue injury to the epiglottis as the ETT passes therethrough. As used herein moving the epiglottis "forward" means in a direction towards the tongue of a subject. When placed at the desired position within the oropharynx, the distal part 125 of the epiglottis elevating bar 120 is arranged to be placed at a position more distal to the tip of the epiglottis. The inventor believes that the epiglottis elevating bar 120 is preferably designed, constructed, shaped, and/or dimensioned to prevent impingement of the distal part 125 of the epiglottis elevating bar 120 with the tip of the epiglottis. One non-limiting example way to prevent such impingement is to position the distal part 125 of the epiglottis elevating bar 120 close to the face 90 of the ramp 76. This may be achieved by one or more of the following non-limiting ways.

In some embodiments, the epiglottis elevating bar 120 is formed of an elastic material. The elastic material may be one or more of silicone, thermoplastic polyurethane, thermoplastic elastomers such as styrene ethylene butadiene styrene, or any other types of polyurethane, polyethylene, and medically compatible polymeric materials. The elasticity or elastic modulus of the material used to form the epiglottis elevating bar 120 may be the same or different from the elastic modulus of the material used to form the blade 14. The elasticity and/or thickness and/or rigidity of the material(s) used to form the epiglottis elevating bar 120 may be adjusted to optimize the placement of the epiglottis elevating bar 120 at a desired downward incline towards the ramp 76 and/or the first face 16 of the blade 14. This may advantageously lower the possibility of impingement of the distal lateral edge 128 of the epiglottis elevating bar 120 with the epiglottis which may result in premature resistance to the advancement of the device 10. This may also prevent the downfolding of the epiglottis while the ETT passes behind the epiglottis elevating bar 120 as this placement may prevent the transfer of energy of the distal tip of the ETT to the epiglottis, particularly when the epiglottis is longer than average. The epiglottis elevating bar 120 may be formed of different material(s) or material(s) comprising different physical properties (e.g., elasticity and/or thickness and/or rigidity) at different regions thereof.

Referring best to FIG. 2B, in some embodiments, the distal part 125 of the epiglottis elevating bar 120 is arranged within the distal conduit 100 by for example rolling downwardly and/or proximally therein during manufacturing of the device 10 and/or at a rest position before use by an operator (e.g., a care provider). This rolling action may advantageously create elastic recoil of the epiglottis elevating bar 120. During use, as the ETT is pushed forwardly through the distal conduit 100 distally in a direction towards the distal tip 70 of the blade 14, the distal tip of the ETT pushes the rolled distal part 125 of the epiglottis elevating bar 120 out of the distal conduit 100, thereby unwinding the rolled epiglottis elevating bar 120, and pressing the epiglottis forwardly and opening the pathway of the ETT through the vocal cords. The elastic recoil of the epiglottis elevating bar 120 thus results in the placement of the distal part 125 of the epiglottis elevating bar 120 close to the face 16 of the blade 14 and the ramp 76. The rolled distal part 125 of the epiglottis elevating bar 120 may be unwounded before use, i.e., before the device 10 is inserted into the mouth of a subject, or during use, i.e., after the device 10 has been inserted into the mouth of the subject, and the ETT advances forwardly through the distal conduit 100 to unwound the rolled distal part 125.

Figure 4:
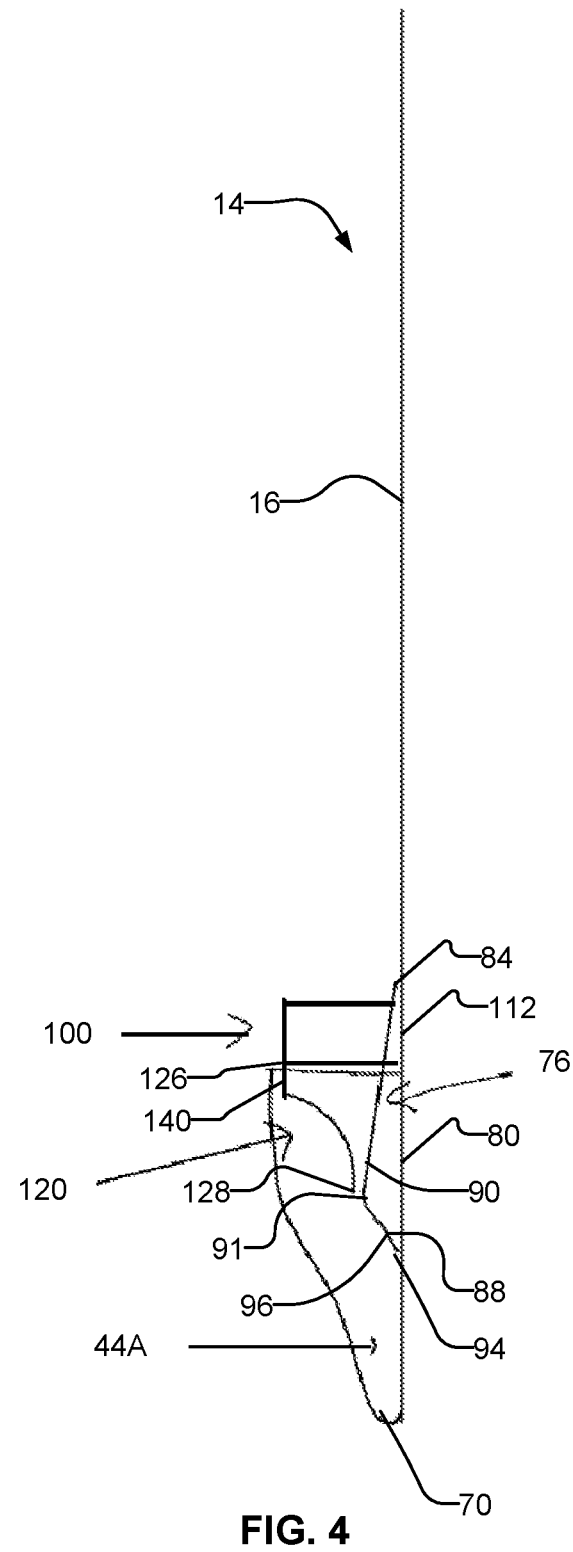
FIG. 4 is a side elevation view of an airway device according to another embodiment of the invention.

Referring best to FIG. 4, in some embodiments, the epiglottis elevating bar 120 extends from the proximal lateral edge 126 that may be joined to the distal conduit 100, along a substantially straight region 140, and therefrom extends to the distal lateral edge 128. The epiglottis elevating bar 120 may for example be arranged to curve inwardly towards the face 90 of the ramp 76 as the bar 120 extends from the substantially straight region 140 to the distal lateral edge 128.

Figure 3:
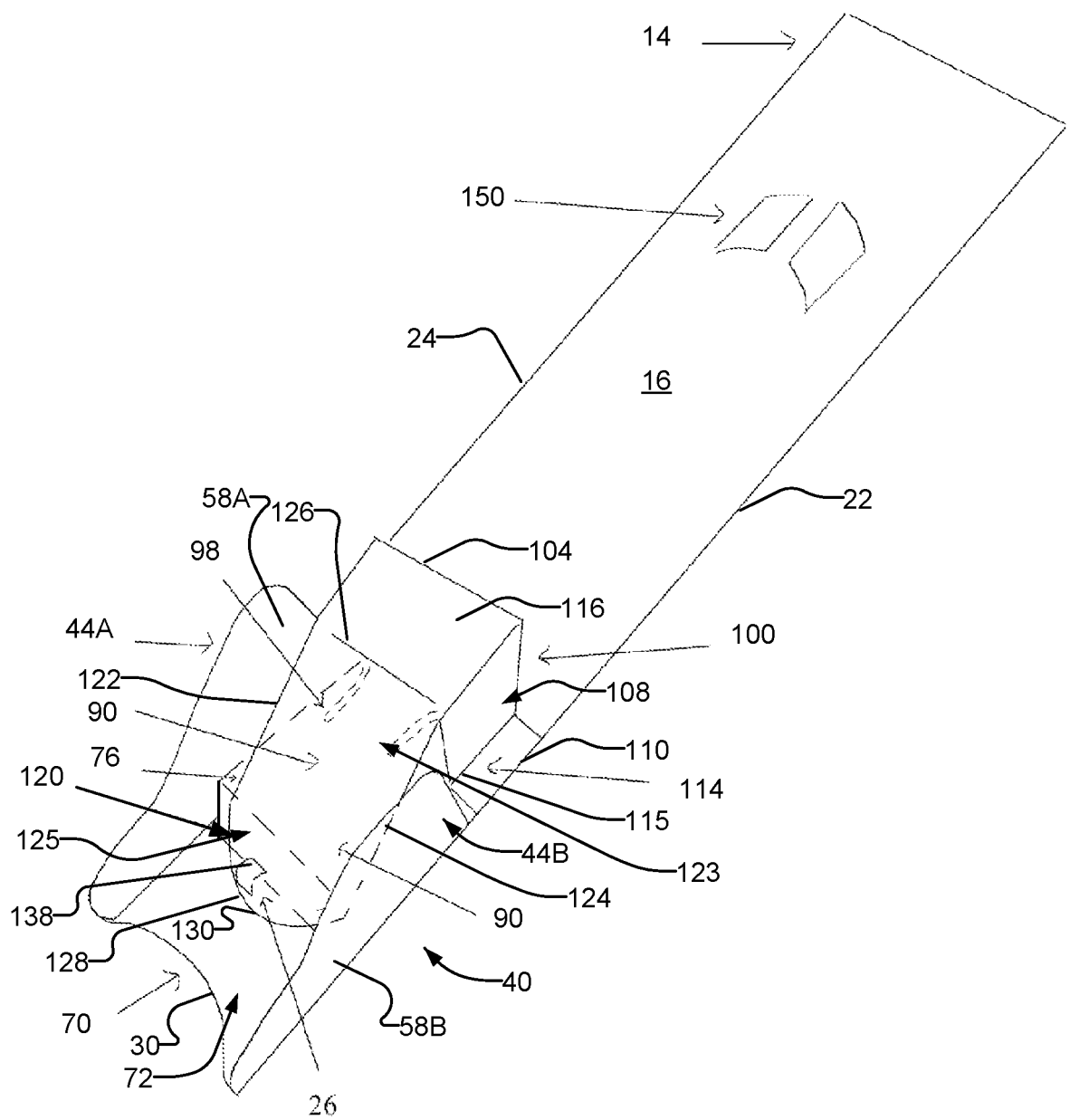
FIG. 3 is a front perspective view of an airway device according to another embodiment of the invention.

As best shown in FIG. 3, in some embodiments, the distal lateral edge 128 of the epiglottis elevating bar 120 is curved inward or outward. In some embodiments, the distal lateral edge 128 curves to define a rounded tip and/or tapered tip of the epiglottis elevating bar 120. A rounded and/or tapered tip may assist to decrease the friction between the ETT and the epiglottis elevating bar 120 while the ETT presses against the bar 120 and unwinds the bar 120. In some embodiments, the distal lateral edge 128 of the epiglottis elevating bar 120 is positioned substantially orthogonal to the first and/or second longitudinal edges 122,124 of the bar 120.

Figure 11:
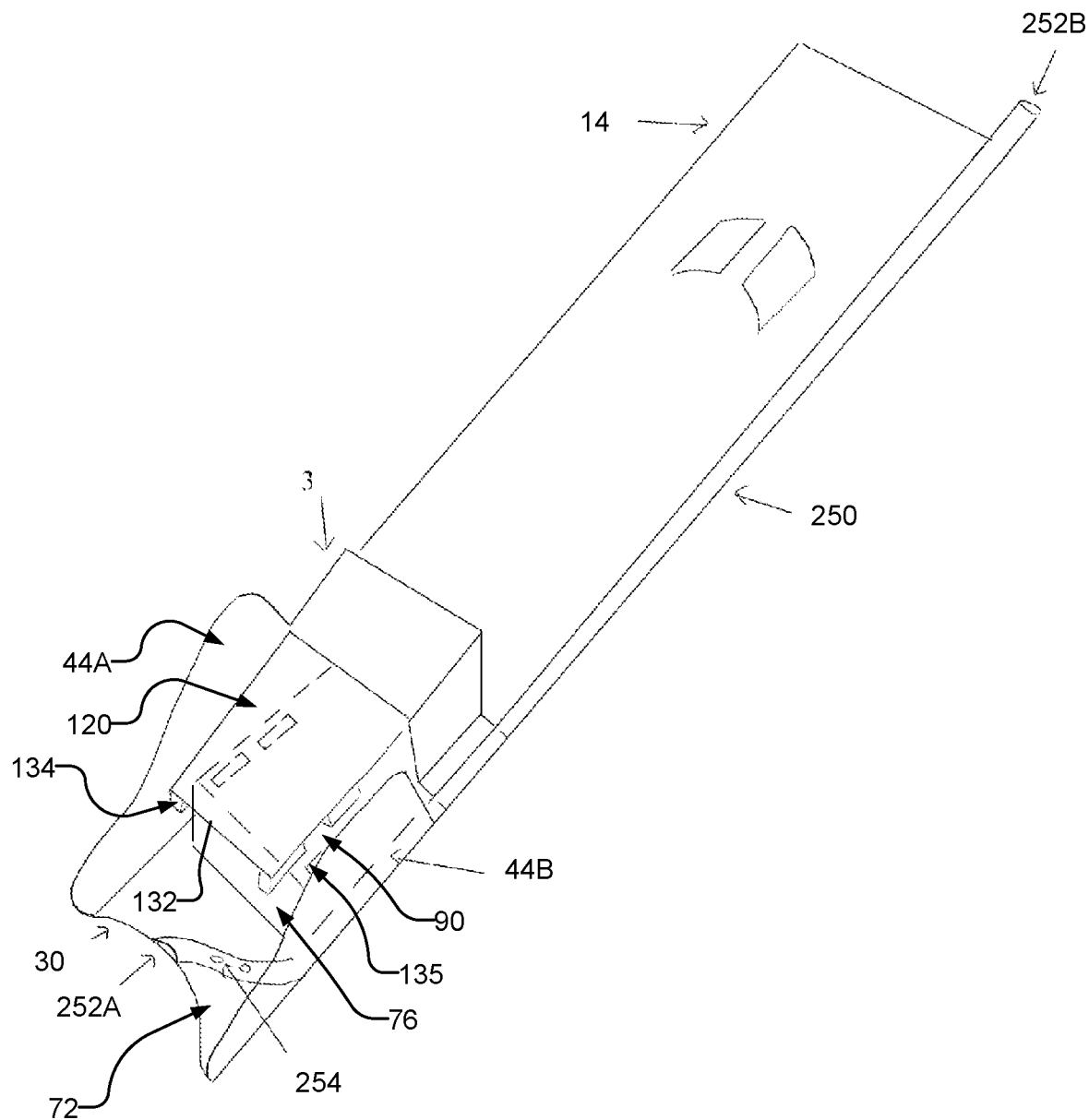
FIG. 11 is a front perspective view of an airway device according to another embodiment of the invention.

Referring best to FIG. 11, in some embodiments, one or more attachment means 134 are arranged at an inner surface 132 of the epiglottis elevating bar 120 so as to secure the epiglottis elevating bar 120 to the face 90 of the ramp 76 and/or to the downward sloping face 96 of the ramp 76 and/or to the first face 16 of the blade 14. Such attachment means 134 may in some embodiments be arranged near the distal part 125 of the epiglottis elevating bar 120, but this is not necessary however. The attachment means 134 may be arranged at any suitable position(s) on the inner surface 132 of the epiglottis elevating bar 120. In some example embodiments, such attachment means 134 comprises one or more strips projecting outwardly from the inner surface 132 of the epiglottis elevating bar 120. The one or more strips may be dimensioned to be snuggly fit within corresponding one or more slots 135 defined on the face 90 of the ramp 76 and/or one or more slots defined on the first face 16 of the blade 14. In such embodiments, the epiglottis elevating bar 120 is arranged to curve inwardly toward the ramp 76 as the bar 120 extends from the proximal lateral edge 126 to the distal lateral edge 128. In some example embodiments, the one or more strips and slots comprises a pair of strips and corresponding slots arranged laterally spaced-apart on the respective epiglottis elevating bar 120 and face 90 of the ramp 76. In other example embodiments, the one or more strips and slots comprises a plurality of pairs of strips and corresponding slots arranged laterally spaced-apart on the respective epiglottis elevating bar 120 and face 90 of the ramp 76. This may facilitate keeping the epiglottis elevating bar 100 close to the ramp 76 for a longer period of time so as to ensure that the device 10 passes behind the epiglottis fully and smoothly.

The dimensions of the one or more strips projecting from the inner surface 132 of epiglottis elevating bar 120 (and the corresponding slots 135 defined on the ramp 76 and/or blade 14) may not be the same. In some embodiments, the height of the one or more strips arranged at one side of the epiglottis elevating bar 120 may be different from the height of the one or more strips arranged at an opposing side thereof. For example, since the distal tip of the ETT is bevel-shaped, in which the tip extends longer on the right side than on the left side, the height of the one or more strips arranged at the left side of the epiglottis elevating bar 120 may be less than the height of the one or more strips arranged at the right side thereof. This may advantageously facilitate detachment of the epiglottis elevating bar 120 at the left side before the distal tip of the ETT at the right side begins to downfold the epiglottis. As used herein, left and right sides refer to the respective left and right sides of the body of a subject at which the device (ETT or device 10) faces when the device is advanced into the body of the subject. Other attachment means 134 may for example comprise one or more magnets on the epiglottis elevating bar 120 arranged for example near the distal part 125 thereof, and on the face 90 of the ramp 76.

Figure 5:
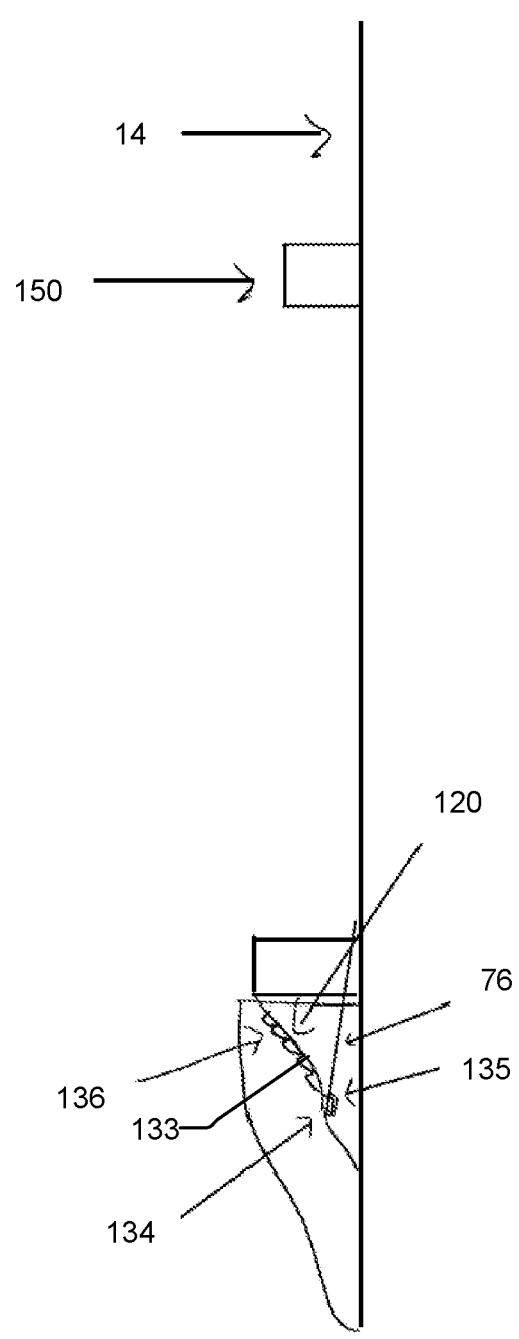
FIG. 5 is a side elevation view of an airway device according to another embodiment of the invention.

Referring best to FIG. 5, in some embodiments, one or more projections 136 (e.g., bumps and the like) extend outwardly from the outer surface 133 of the epiglottis elevating bar 120, opposite to the inner surface 132 thereof. Such projections may facilitate advancement of the epiglottis forward and/or increase the distance between the epiglottis and the ramp 76 as the device 10 is being advanced into the oropharyngeal cavity, thereby advantageously minimizes the possibility of downfolding of the epiglottis during advancement of the device 10 and/or the ETT.

Figure 6:
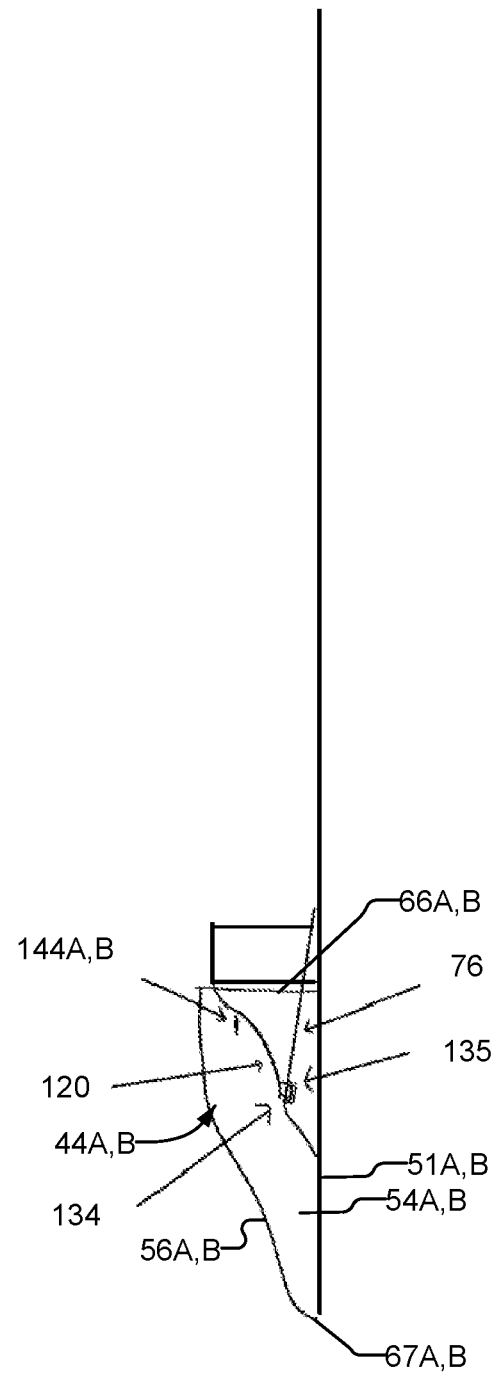
FIG. 6 is a side elevation view of an airway device according to another embodiment of the invention.
Figures 7, 8:
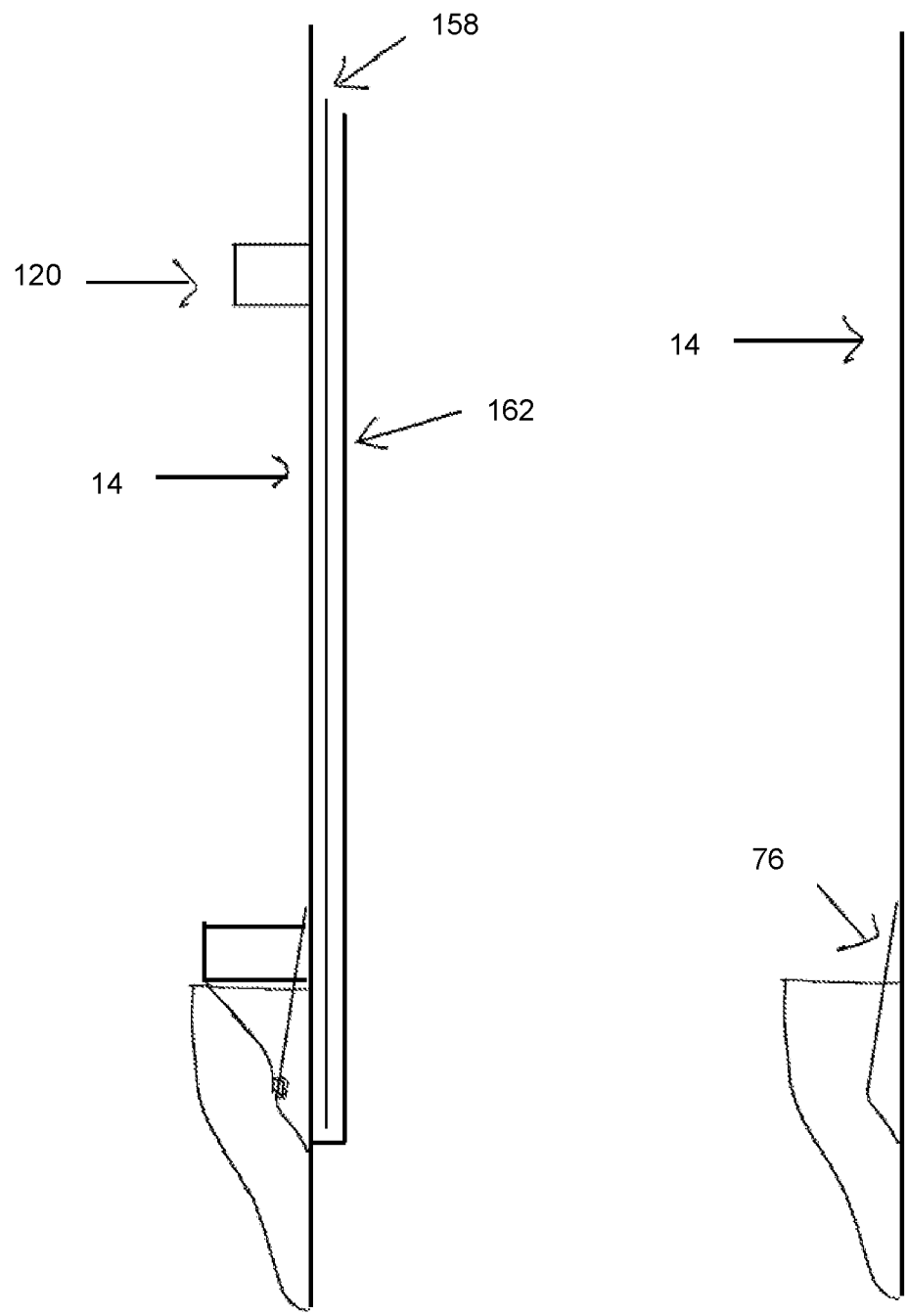
FIG. 7 is a side elevation view of an airway device according to another embodiment of the invention.
FIG. 8 is a side elevation view of an airway device according to another embodiment of the invention.

Referring best to FIG. 6, in some embodiments, a shelf 144A,B is arranged to project outwardly from each of the walls 54A,B of the side components 44A,B towards the ramp 76. The shelves 144A,B may be positioned at a point of the walls 54A,B between the first and second longitudinal side 51A,B, 56A,B of the side components 44A,B. The point may be positioned closer to the proximate lateral side 66A,B than the distal lateral side 67A,B of the side components 44A,B. The shelves 144A,B projecting from the pair of side components 44A,B may be arranged in mirror image symmetry to one another with respect to the central longitudinal axis of the blade 14.

Referring best to FIG. 3, in some embodiments, one or more attachment means 138 are secured to the first face 16 of the blade 14 (e.g., positioned distally to the ramp 76 along the longitudinal axis of the blade 14), and/or on the ramp 76 (e.g., at ramp longitudinal sides 80, 84), arranged to attach to the distal part 125 of the epiglottis elevating bar 120. The one or more attachment means 138 may comprise a hook and/or loop and hoop, elastic bands, magnets, springs, or a similar fastener. Other methods for securing the distal part 125 of the epiglottis elevating bar 120 to the ramp 76 and/or the first face 16 of the blade 14 so as to keep the epiglottis elevating bar 120 close to blade 14 and/or the ramp 76 are within the scope of the invention. Keeping the epiglottis elevating bar 120 close to the blade 14 and/or the ramp 76 may also keep the epiglottis elevating bar 120 close to the ETT, which may advantageously facilitate exchanging the ETT or facilitate passing a suction line beside the ETT while the ETT is in the trachea so as to suction the secretions above the ETT cuff in order to prevent ventilator associated pneumonia.

In some embodiments, a proximal conduit 150 is arranged at the proximal region 38 of the blade 14, proximal to the side components 44A,B along the longitudinal axis of the blade 14. In some embodiments, the proximal conduit 150 comprises a pair of laterally spaced-apart arms 154 joined to the first face 16 of the blade 14 and projecting outwardly therefrom to define a channel 156 dimensioned for an ETT to pass therethrough. In some embodiments, the channel 156 is positioned along a central longitudinal axis of the blade 14. The proximal conduit 150 may alternatively comprise a hollow tube which defines the channel 156. The proximal conduit 150 may be directly joined to the first face 16 of the blade 14, or indirectly joined thereon (e.g., by securing to a base which may be joined to the first face 16 of the blade 14). The proximal conduit 150 may advantageously facilitate the preloading of the device 10 with the ETT to speed up the process of intubation and/or decrease the contact of the ETT with the tongue of the subject.

Referring best to FIG. 9, in some embodiments, a rail 162 is arranged on the second face 17 of the blade 14. The rail 162 may define an elongated channel 164 within which a second blade 158 may be inserted and moved along the longitudinal axis of the blade 14. In some embodiments, the rail 162 comprises a first longitudinal rail arm 166 arranged adjacent to the first longitudinal edge 22 of the blade 14, and a second longitudinal rail arm 168 laterally spaced from the first longitudinal rail arm 166, arranged adjacent to the second longitudinal edge 24 of the blade 14. One or more lateral rail arms 170 may be arranged to connect the first longitudinal rail arm 166 to the second longitudinal rail arm 168. In some embodiments, one of the lateral rail arms 170A connects the first longitudinal rail arm 166 to the second longitudinal rail arm 168 at distal ends 172A,B of the first and second longitudinal rail arms 166,168. In some embodiments, another one of the lateral rail arms 170B connects the first longitudinal rail arm 166 to the second longitudinal rail arm 168 at a point between the distal ends 172A,B and proximal ends 176A,B of the first and second longitudinal rail arms 166,168. The point may be at a midpoint along the longitudinal lengths of the first and second longitudinal rail arms 166,168. Any number of lateral rail arms 170 may be arranged to connect the first and second longitudinal rail arms 166,168 at any suitable positions along the lengths thereof. The rail 162 may alternatively be arranged at any suitable position on the first face 16 of the blade 14. Any other suitable configurations of the rail 162 which forms a suitable dimensioned channel 164 is within the scope of the invention. For example, the rail 162 may comprise an open-end pocket with the elongated channel 164 defined within for receiving the second blade 158.

In addition to providing a channel through which the second blade 158 may be inserted and moved therein, the rail 162 may also serve as an indicator for placement of the device 10 within the mouth of the subject. For example, the first and second longitudinal rail arms 166, 168 may be placed between the canine teeth which serves as an indicator that the device is placed in the midline of the mouth of the subject. The rail 162 may also provide the user an estimate of the appropriateness of the size of the device 10 for the particular subject.

In some embodiments, the second blade 158 comprises a reinforcing blade. The reinforcing blade may assist to increase the stiffness and/or stability of the proximal region 38 of the blade 14, which may advantageously facilitate the passage of the device 10 through the mouth of the subject, and/or to ensure that the distal tip 70 of the blade 14 has reached a desired position within the oropharyngeal cavity where there is no further room for advancement. The reinforcing blade may be moveable within the channel 164 of the rail 162. In other example embodiments, the reinforcing blade is joined or adhered or otherwise secured onto the first 16 and/or second face 17 of the blade 14. The reinforcing blade may for example comprise a configuration similar to the blade 14. For example, the reinforcing blade may comprise an elongated body having opposing first and second longitudinal edges and opposing first and second lateral edges each connecting the first to the second longitudinal edge at opposite lateral sides of the body. In some embodiments, the elongated body is substantially flat. The elongated body may in some example embodiments have a rectangular shape. The reinforcing blade may be formed of any suitable material or combination of materials such as any medically compatible polymeric materials. The material(s) which forms the reinforcing blade may have a flexural modulus that is greater than the material(s) which forms the blade 14. The reinforcing blade may extend along the entire longitudinal length of the blade 14, or a portion of the entire length of the blade 14.

Figure 12A:
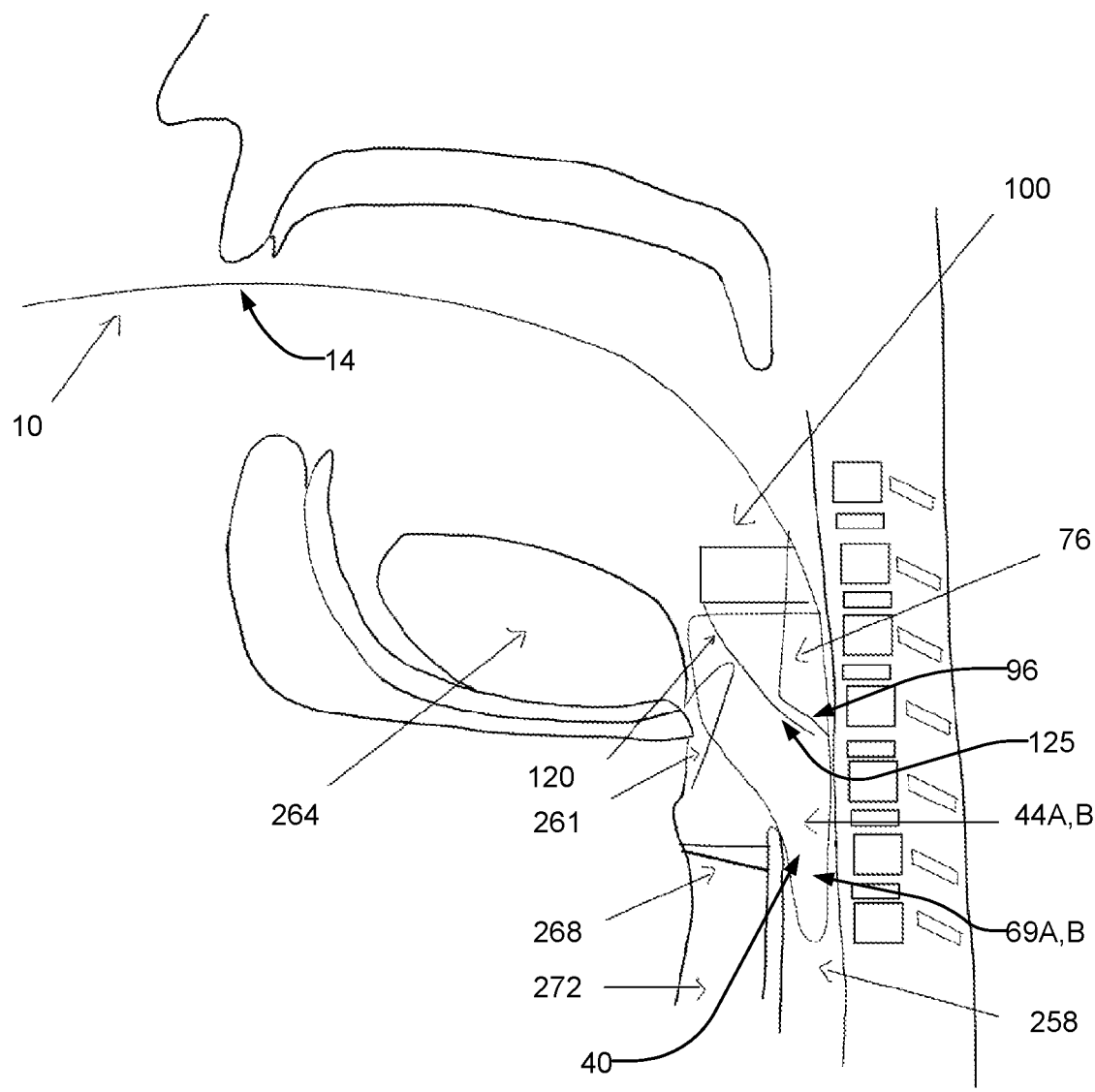
FIG. 12A is a schematic diagram illustrating an airway device advanced into the oropharyngeal cavity according to an example embodiment of the invention.
Figure 12B:
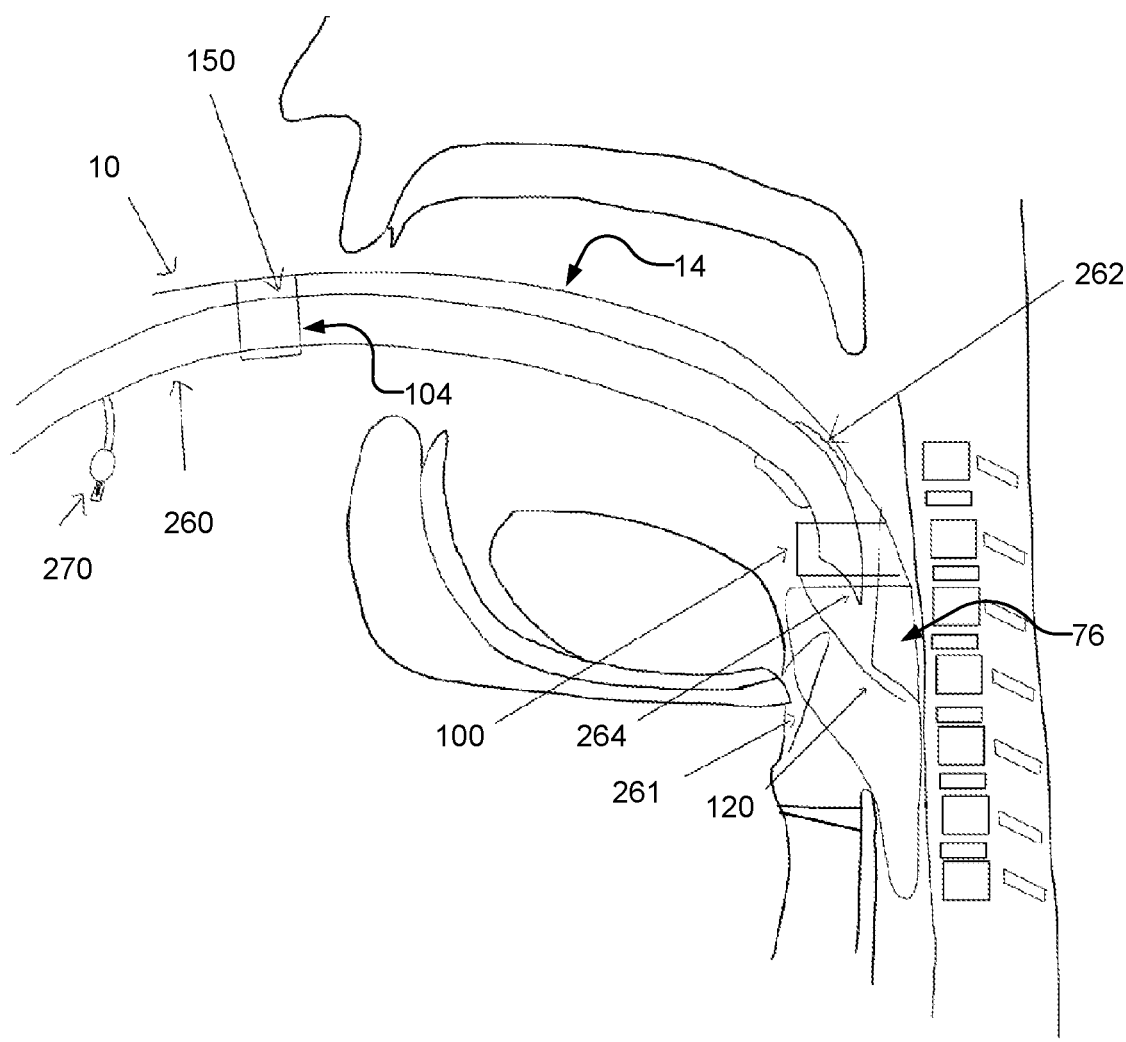
FIG. 12B is a schematic diagram illustrating an endotracheal tube (ETT) arranged on the airway device shown in FIG. 12A.

An example method of use of the FIGS. 1-11 embodiment is as follows. Referring to the schematic diagrams in FIGS. 12A to 12D, the device 10 is inserted into a mouth of a subject. The device 10 is passed through the mouth until a resistance is felt where the distal region 40 of the blade 14 is placed in the desired position within the oropharyngeal cavity. When the device 10 is in the desired position, the distal regions 69A,B of the side components 44A,B rest in the upper esophagus 258 and the distal conduit 100 rests on top of the epiglottis 261 and between the tongue 264 and the posterior pharyngeal wall. FIG. 12A illustrates an embodiment in which the distal part 125 of the epiglottis elevating bar 120 is placed close to the blade 14 and the downward sloping face 96 of the ramp 76 and behind the epiglottis 261. In embodiments in which the epiglottis elevating bar 120 is rolled proximally within the distal conduit 100 before advancement, the epiglottis elevating bar 120 is oriented above the epiglottis 261.

Figure 12C:
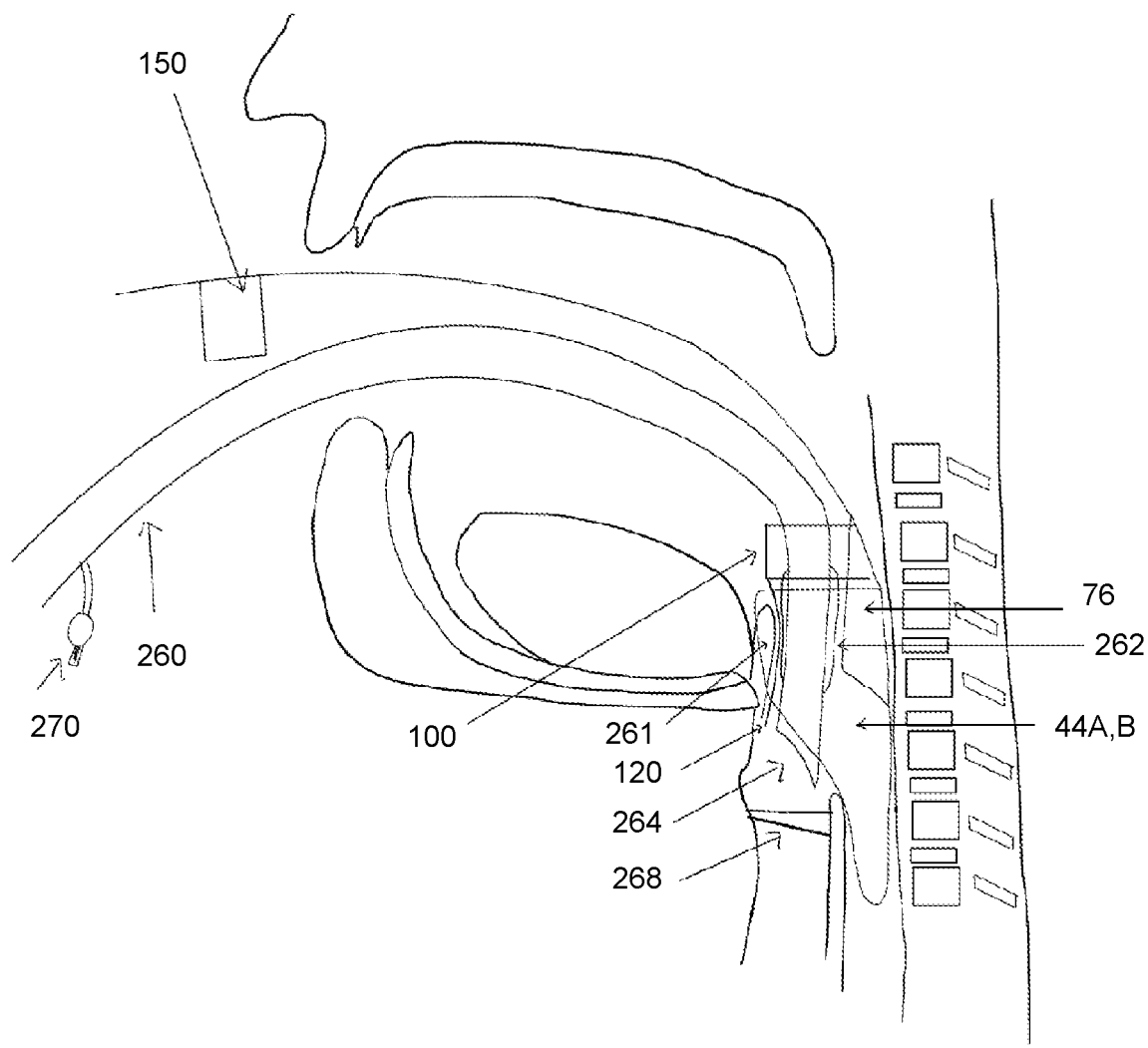
FIG. 12C is a schematic diagram illustrating the ETT and the airway device shown in FIG. 12B with the ETT advanced further into the oropharyngeal cavity according to an example embodiment of the invention.
Figure 12D:
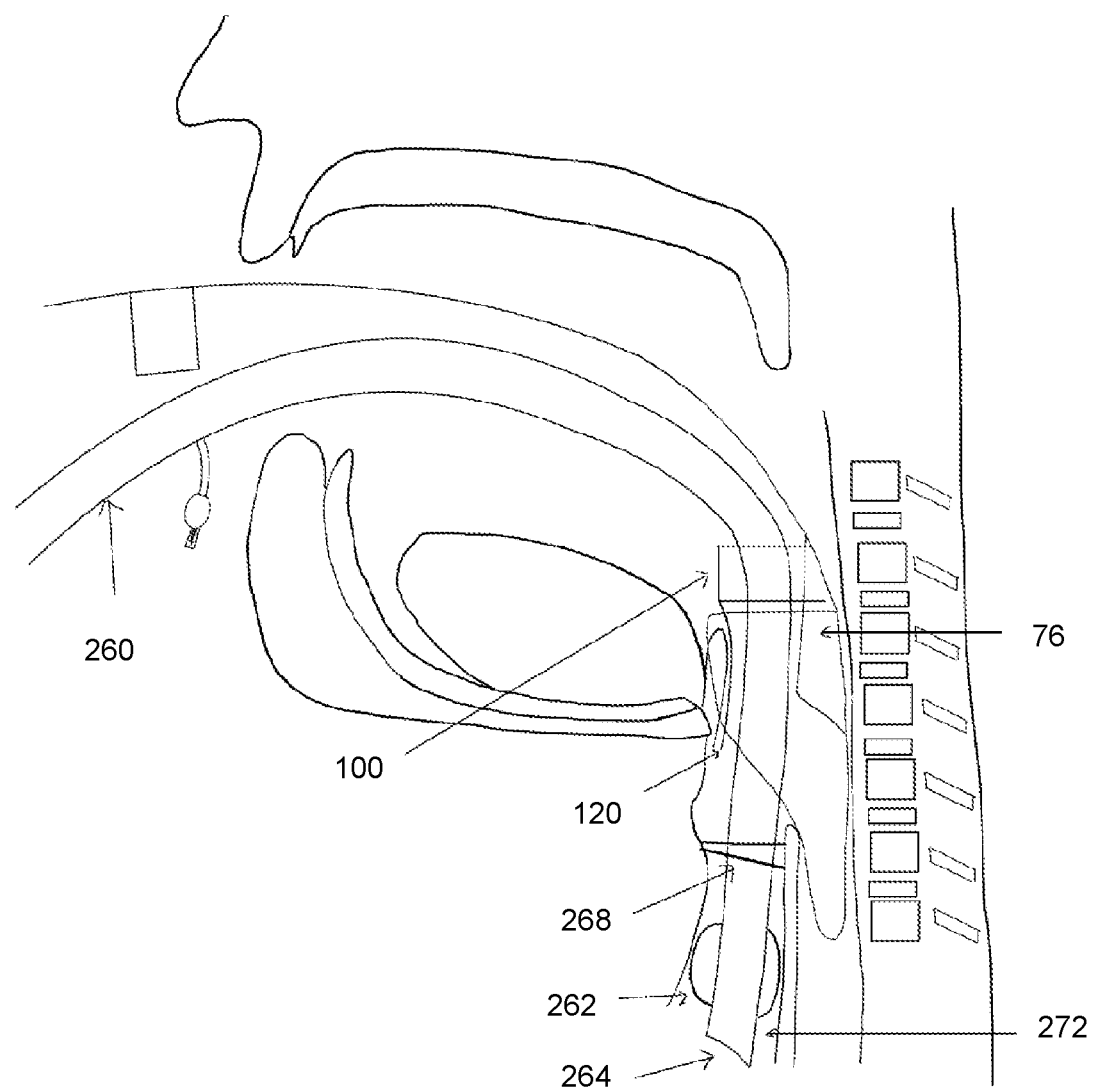
FIG. 12D is a schematic diagram illustrating the ETT and the airway device shown in FIG. 12C with the ETT advanced even further into the oropharyngeal cavity according to an example embodiment of the invention.

Once the device 10 is advanced to the desired position, an ETT 260 may be arranged on the blade 14 for advancement into the oropharyngeal cavity. The cuff 262 of the ETT 260 may be deflated during advancement. In some embodiments, a distal part 264 of the ETT 260 may be placed within the distal conduit 100 arranged to pass through the channel 104. The proximal part of the ETT 260 may be secured within the proximal conduit 150. The ETT may then be pushed distally along the longitudinal axis of the blade 14 to pass through the channel 104 of the distal conduit 100 towards the epiglottis elevating bar 120. The ETT 260 may then be advanced over the ramp 76, thereby pushing the epiglottis forwardly. Once the distal part 264 of the ETT 260 is positioned above the vocal cords 268, the cuff 262 of the ETT 260 is inflated partially or fully by an ETT pilot bladder 270, thereby creating a seal below the distal conduit 100. The distal conduit 100, the ramp 76, the side components 44A,B and the epiglottis elevating bar 120 may surround the cuff 262, creating the seal to prevent leakage of air towards the mouth, and thus achieving effective supraglottic ventilation. The proximal end of the ETT 260 may be connected to a bag or ventilator for performing supraglottic ventilation. This may be especially helpful in situations in which passing the ETT 260 through the vocal cords 268 may be challenging. Performing supraglottic ventilation in such a way may assist with maintaining oxygenation and ventilation. Once the ETT 260 is advanced, the proximal part thereof may slide out of the proximal conduit 150 as shown in FIG. 12C. In embodiments in which the epiglottis elevating bar 120 and/or the ramp 76 and/or the first face 16 of the blade 14 comprises strips, slots, hook, and the like for securing the distal part 125 of the bar 120 thereto, the advancement of the ETT 260 between the epiglottis elevating bar 120 and the ramp 76 may detach any attachment means connected to the epiglottis elevating bar 120. In embodiments in which the distal part 125 of the epiglottis elevating bar 120 is rolled proximally within the distal conduit 100, the advancement of the ETT 260 between the epiglottis elevating bar 120 and the ramp 76 unwinds the rolled distal part 125 thereof.

The ETT 260 may be advanced further, passing through the vocal cords 268. The distal part 264 of the ETT 260 may be positioned inside the trachea 272. Once the ETT 260 is in the trachea 272, the cuff 262 may be inflated. The distal conduit 100 and/or the ramp 76 may assist in guiding the distal part 264 of the ETT 260 anteriorly and towards the vocal cords 268. In embodiments in which the ramp 76 comprises strips or guiding plates 98, such components may assist with preventing and/or reducing undesired lateral (e.g., left and right) displacement of the ETT 260. After the ETT is positioned inside the trachea, the ETT may be held by the operator's hand, and the device 10 may then be taken out of the mouth of the subject, and over the ETT, unless there is a need to keep the device 10 in place for a period of time.

FIGS. 13-24 illustrate another embodiment of the invention. The FIGS. 13-24 embodiments of the invention comprises a blade 14 that is substantially similar to the blade 14 as discussed above in respect of the FIGS. 1-11 embodiments with the exception of optionally including of one or both of an elongated slot 178 defined thereon and a base guiding plate 180. The elongated slot 178 and the base guiding plate 180 may be arranged at the distal plate region 72 of the blade 14. In some embodiments, the elongated slot 178 is arranged to extend laterally at a point 182 along the lateral axis of the blade 14 between the side components 44. The point 182 may be positioned between the proximal and distal lateral edges 66A,B, 67A,B of the side components 44A,B. In embodiments in which a ramp 76 is arranged on the blade 14, the elongated slot 178 may be positioned distal to the distal ramp lateral side 88 along the longitudinal axis of the blade 14. In some embodiments, the elongated slot 178 is positioned adjacent to the distal ramp lateral side 88 along the longitudinal axis of the blade 14. The elongated slot 178 may be dimensioned and/or shaped for a roll-down blade 200 to insert and pass therethrough (the roll-down blade 200 will be discussed in detail below). In some embodiments, the elongated slot 178 comprises a width and height that is greater than a width and height of the roll-down blade 200 so as to allow the roll-down blade 200 to insert and pass therethrough.

In such embodiments, the side components 44 are substantially similar to the side components 44 as discussed above in respect of the FIGS. 1-11 embodiments with the exception of optionally including a cleft 184A,B defined on the wall 54A,B of each of the side components 44A,B. The clefts 184A,B may be arranged in mirror image symmetry with respect to the central longitudinal axis of the blade 14. The clefts 184A,B may extend orthogonal to the first face 16 of the blade 14 from the first longitudinal edge 51A,B to the second longitudinal edge 56A,B, or between the first and second longitudinal edges 51A,B, 56A,B of the side components 44A,B. The clefts 184A,B may be positioned at a region 188A,B between the proximal and distal lateral edges 66A,B, 67A,B of the side components 44A,B. In some embodiments, the region 188A,B is positioned at, near, or extends along a region encompassing the point 182. In some embodiments, the clefts 184A,B is positioned at a midpoint between the proximal and distal lateral edges 66A,B, 67A,B of the side components 44A,B. The clefts 184A.B may be dimensioned to surround one or both of lateral edges of the elongated slot 178 and opposing longitudinal sides of the roll-down blade 200 or the distal sliding portion 216, when the roll-down blade 200 is arranged to pass through the elongated slot 178. The clefts 184A,B and/or the base guiding plate 180 may facilitate to orient the sliding distal portion 216 in a substantially or completely horizontal position (or substantially orthogonal relative to the first face 16 of the blade) when the sliding distal portion 216 is extended distally through the elongated slot 178.

The roll-down blade 200 may in some embodiments be formed of a flexible medically compatible polymer which may be more rigid than the material(s) used in manufacturing the blade 14 and/or the side components 44A,B. In some non-limiting example embodiments, the roll-down blade 200 is formed of a material comprising high density polyethylene (HDPE).

Additional one or more clefts may be arranged along the wall 54A,B of each of the side components 44A,B. In some example embodiments, an additional one or more clefts are arranged to join the respective cleft 184A,B vertically along the wall 54A,B, orthogonal to the first face 16 of the blade 14. In such embodiments, the additional one or more clefts may be positioned more proximate to the first face 16 of the blade 14. The additional one or more clefts may comprise a width greater than the width of the clefts 184A,B.

In some embodiments, a base guiding plate 180 is arranged to project distal to the elongated slot 178 along a longitudinal axis of the blade 14. In some embodiments, the base guiding plate 180 is oriented orthogonal to the first face 16 of the blade 14. In some embodiments, the base guiding plate 18 is oriented at an incline with respect to the first face 16 of the blade 14 (see e.g., FIG. 17A). In such embodiments, the base guiding plate 180 comprises an upward sloping face 181 extending towards the first face 16 of the blade 14. In some embodiments, a guide 190 is secured to the distal ends 172A,B of the first and second longitudinal rail arms 166,168 at a first end (not shown) of the guide 190, and to the base guiding plate 180 at the opposing second end 191B. The guide 190 may comprise a curved region 192 with an upward sloping face 194 extending from the second end 191B to the first end thereof. In some embodiments, a cleft 187 is defined on the base guiding plate 180 at a lateral edge 193 thereof (see e.g., FIG. 17B). The cleft 187 may be positioned between opposing longitudinal edges 194A,B of the base guiding plate 180. The cleft 187 may assist with reducing the risk of impingement of the distal plate 224 of the roll-down blade 200 with the epiglottis and/or reducing issues with advancement and/or placement of the device 10 within the laryngopharynx. In some embodiments, a ramp 196 may be arranged to project outwardly from an upper face 195 of the base guiding plate 180 (see e.g., FIG. 17C). The ramp 196 may be positioned adjacent to the lateral edge 193. The ramp 196 may comprise an upward sloping face 197 towards the lateral edge 193 thereof. In some embodiments, the cleft 187 and/or the ramp 196 are positioned along a central lateral axis of the base guiding plate 180. In some embodiments, the lateral edge 193 of the base guiding plate 180 is sloped distally, which may facilitate with directing the ETT towards the trachea.

In some embodiments, a ramp may be arranged proximal to the base guiding plate 180. In some embodiments, the ramp is positioned within the channel 104 of the conduit 100. In some embodiments, a ramp may be positioned distal to the base guiding plate 180. The ramp may facilitate with guiding the ETT towards the trachea during advancement.

Figures 20, 21:
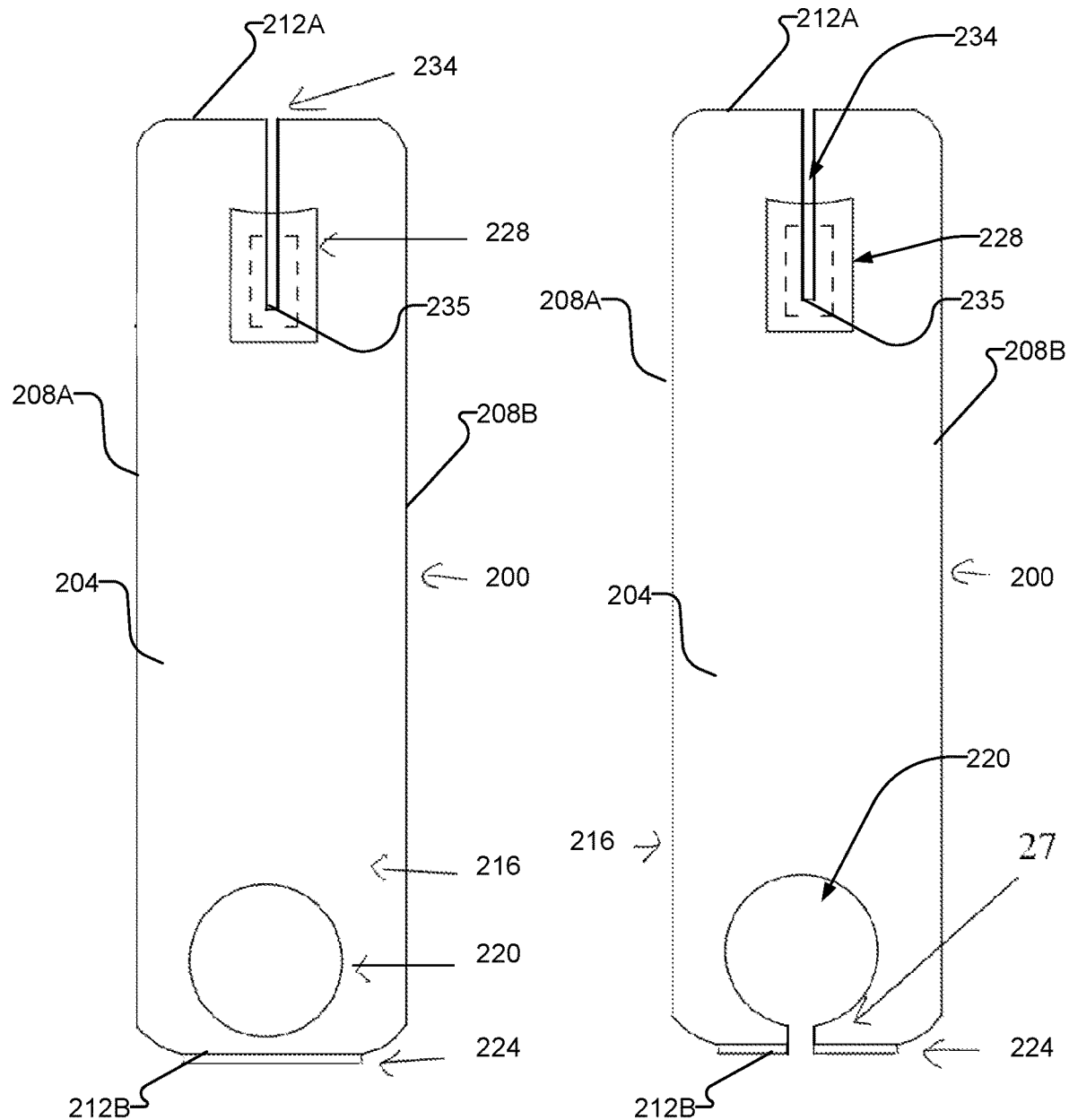
FIG. 20 is a front elevation view of a roll-down blade according to an example embodiment of the invention.
FIG. 21 is a front elevation view of a roll-down blade according to another example embodiment of the invention.
Figure 22:
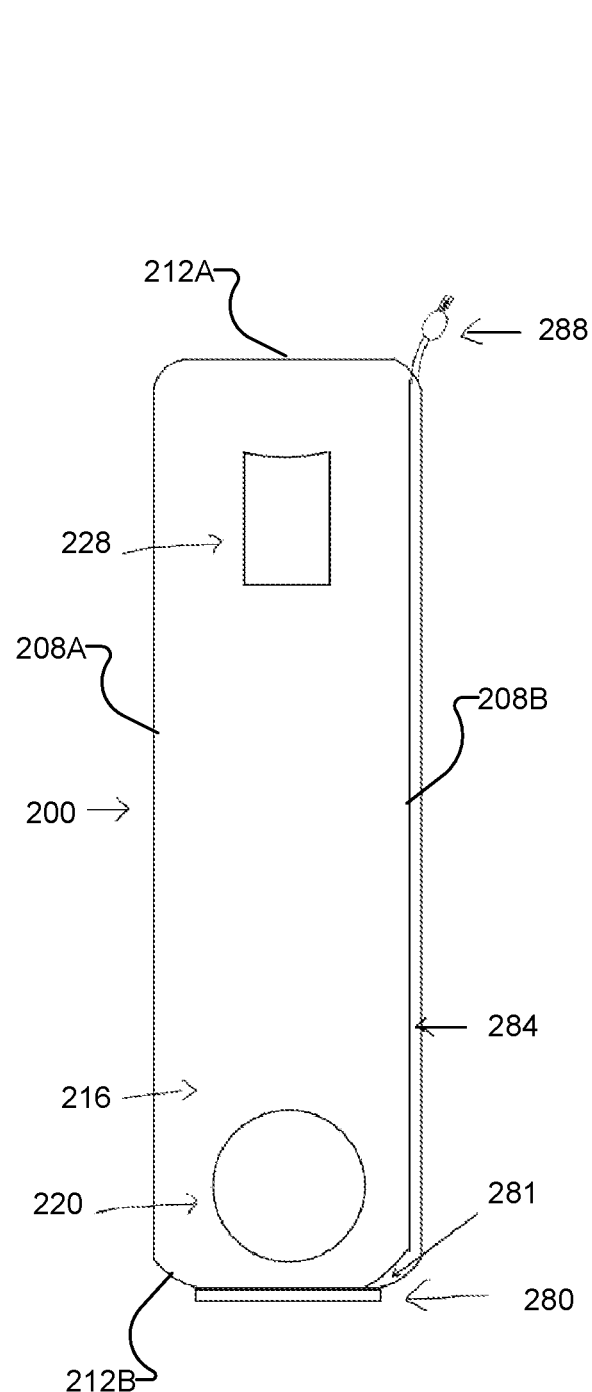
FIG. 22 is a front elevation view of a roll-down blade according to another example embodiment of the invention.

The roll-down blade 200 may be inserted into the rail 162, and is moveable along a longitudinal axis of the blade 14 therein. Non-limiting examples of a roll-down blade 200 are illustrated in FIGS. 20 and 21. The roll-down blade 200 may comprise an elongated body 204 having opposing first and second longitudinal sides 208A,B, and opposing proximal and distal lateral side 212A,B each connecting the first to the second longitudinal side 208A,B at opposite sides of the body 204. The roll-down blade 200 comprises a distal sliding portion 216 near the distal lateral side 212B. The distal sliding portion 216 is adapted to push the epiglottis forward as the distal sliding portion 216 extends distally along the longitudinal axis of the blade 14 through the elongated slot 178. In some embodiments, a central passage 220 is defined on the distal sliding portion 216, dimensioned for an ETT to pass therethrough. In some embodiments, the central passage 220 may be defined by inclined edges, sloping upwardly towards the distal lateral edge 212B of the roll-down blade 200. The inclined edges may assist with directing the ETT towards the trachea as the ETT passes through the central passage 220. Other ways to create an upward slope for guidance of the ETT towards the trachea as the ETT passes through the central passage 220 may be used, for example, creating extending ramps which project outwardly from the face of the edges and/or changing the shape of the central passage 220 by blocking parts of the central passage 220 (e.g., a posterior region thereof), and/or providing a second roll-down blade and sliding the blade within the same rail 162 or a second rail during advancement, in coordinated movement with the roll-down blade 200. The distance between the central passage 220 and the distal lateral edge 212B of the roll-down blade 200 may be adjusted to optimize passage of the ETT into the trachea during advancement of the ETT through the central passage 220.

In some embodiments, the distal sliding portion 216 comprises rounded and/or curved edges so as to prevent exerting pressure and/or inducing any injury to the pharyngoepiglottic fold. In some embodiments, the proximal lateral sides 212A,B of the roll-down blade 200 comprise opposing round and/or curved edges and/or wide, laterally protruded, edges, and in some other embodiments, the proximal and/or distal lateral sides 212A,B of the roll-down blade 200 comprise opposing straight edges.

In some embodiments, a distal plate 224 is secured to the distal lateral side 212B of the body 204. The distal plate 224 may be oriented orthogonal to the body 204. In some embodiments, the distal plate 224 is positioned along a central longitudinal axis of the blade 14. In some embodiments, the distal plate 224 and the distal sliding portion 216 and/or the rest of the body of the roll-down blade 200 are integrally formed. In some embodiments, the distal plate 224 is directly or indirectly attached to the distal sliding portion 216 by mechanical means such as a screw and a plug, rivets, staples, wires, etc. In some other embodiments, the distal plate 224 is joined to the distal sliding portion 216 by heat welding, adhesive means, etc.

In some embodiments, a cleft extends from the distal lateral edge 212B of the roll-down blade 200 to the central passage 220, thereby creating a gap in the distal lateral edge 212B, separating the distal lateral edge 212B into two spaced-apart portions (see FIG. 21). A cleft may also separate a distal plate 224 which may be securable to the distal lateral edge 212B into two spaced-apart portions. Such a cleft facilitates the removal of the device 10 after the ETT is placed in the trachea. In some embodiments, one or more holes may be defined on the surface of the roll-down blade 200, proximate to the distal lateral edge 212B, configured to allow a string to pass therethrough, for joining the sides of the cleft during insertion of the device 10, and/or further facilitating the removal of the device 10 from the ETT.

Figure 13A:
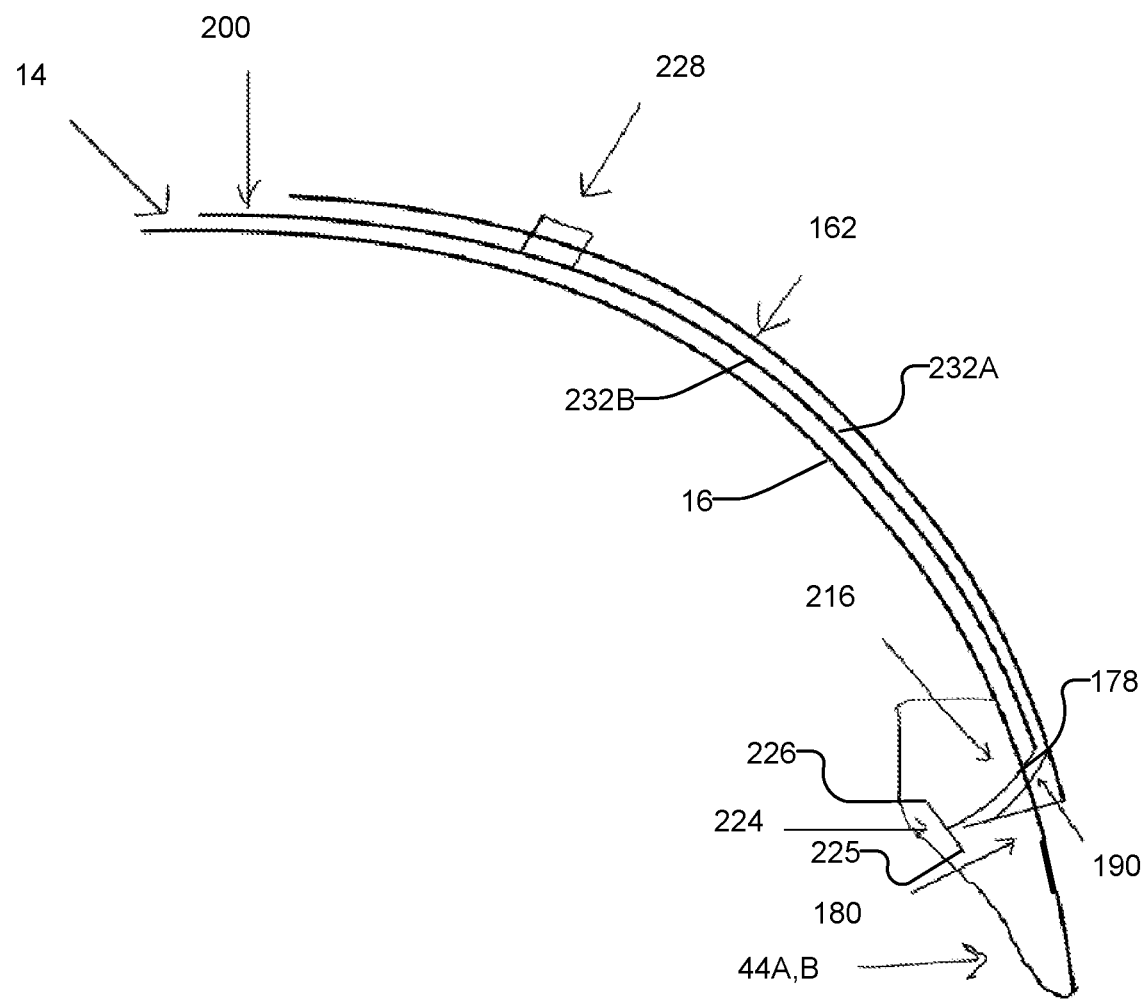
FIG. 13A is a side elevation view of an airway device according to another embodiment of the invention, with a sliding distal portion of a roll-down blade shown in a rest position.
Figure 13B:
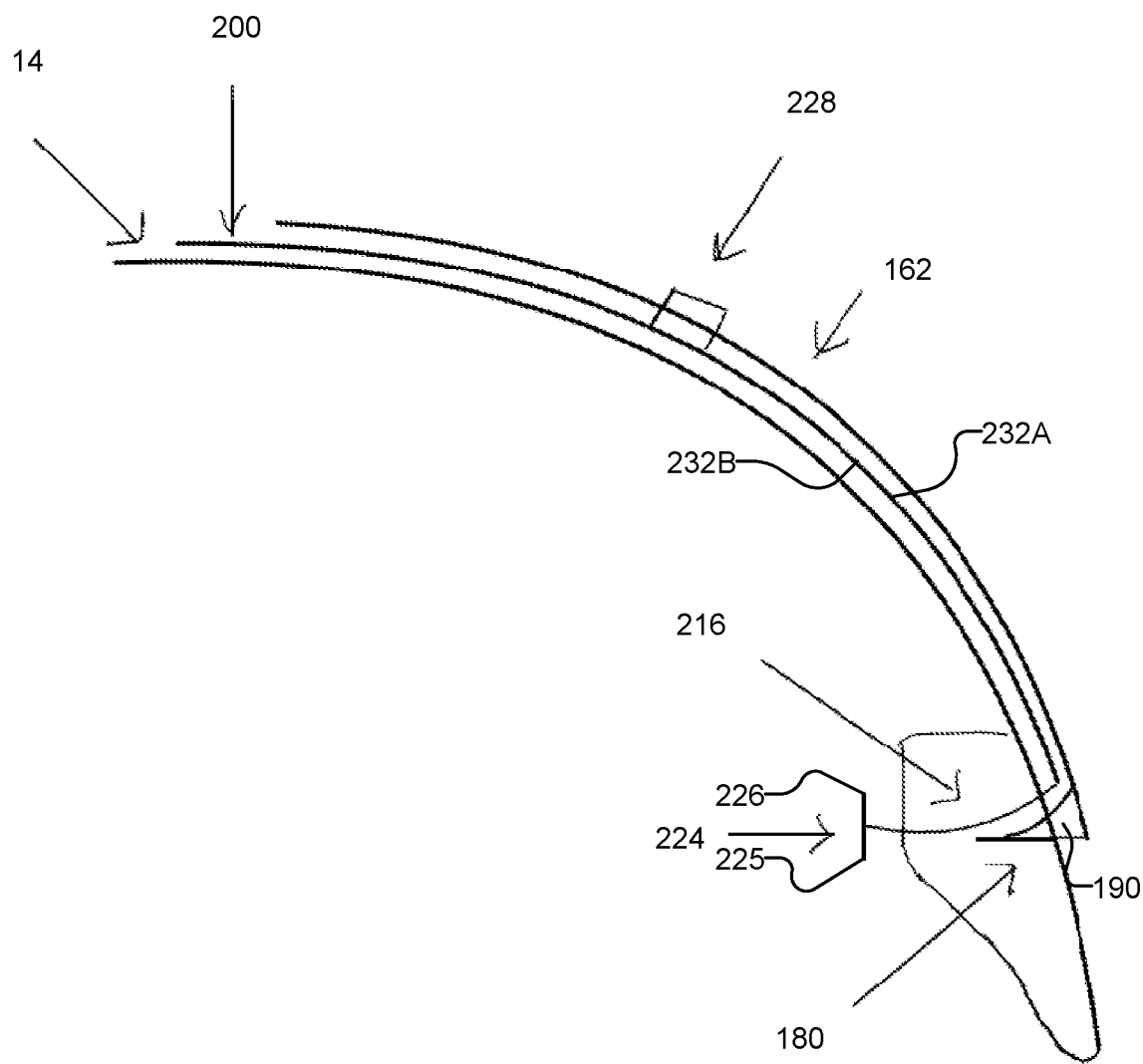
FIG. 13B is a side elevation view of the FIG. 13A airway device, with the sliding distal portion of the roll-down blade shown in an extended position.
Figure 13C:
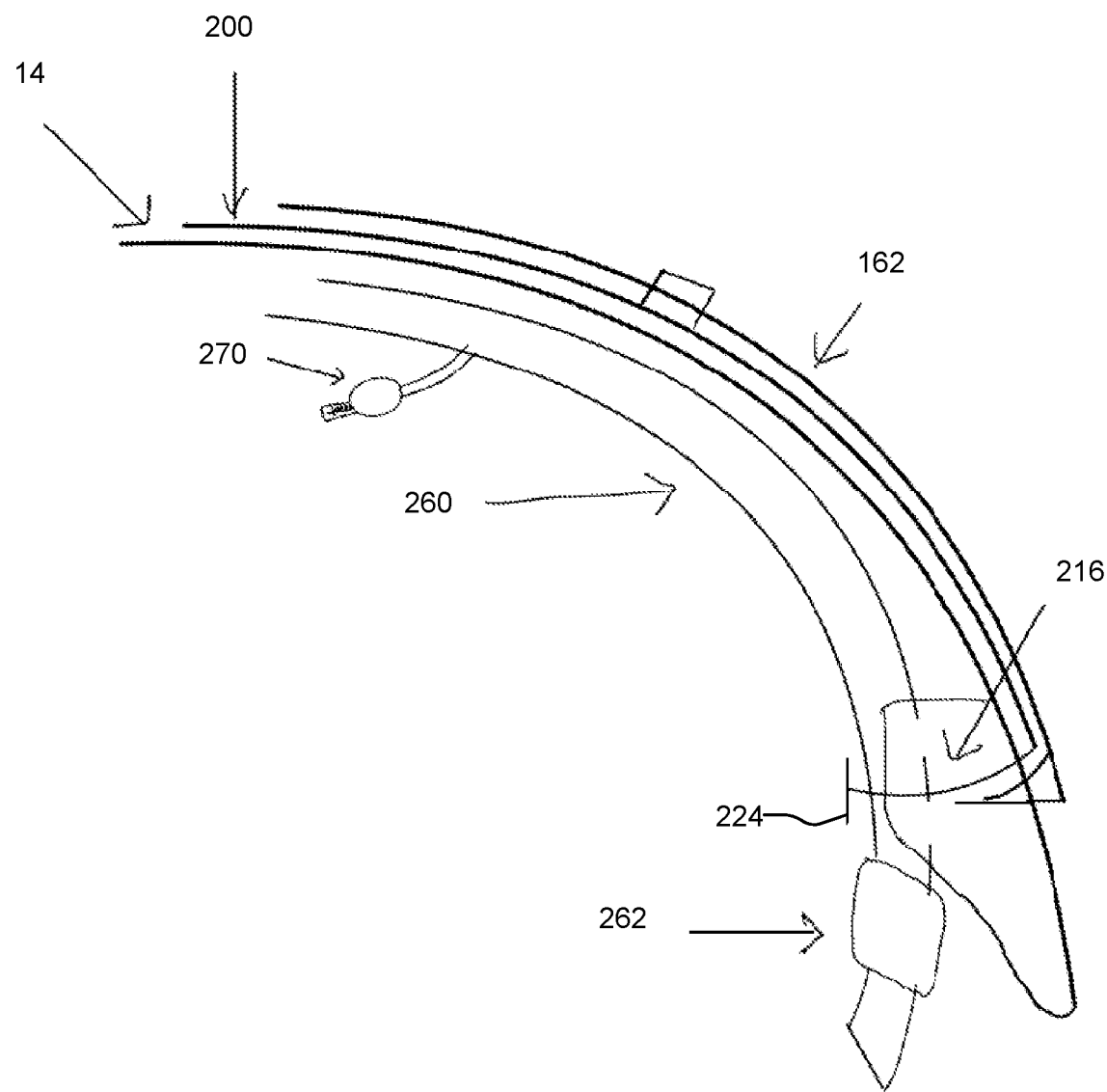
FIG. 13C is a side elevation view of the FIG. 13B airway device, with an ETT passed through a central passage of the sliding distal portion of the roll-down blade.
Figures 14A, 14B:
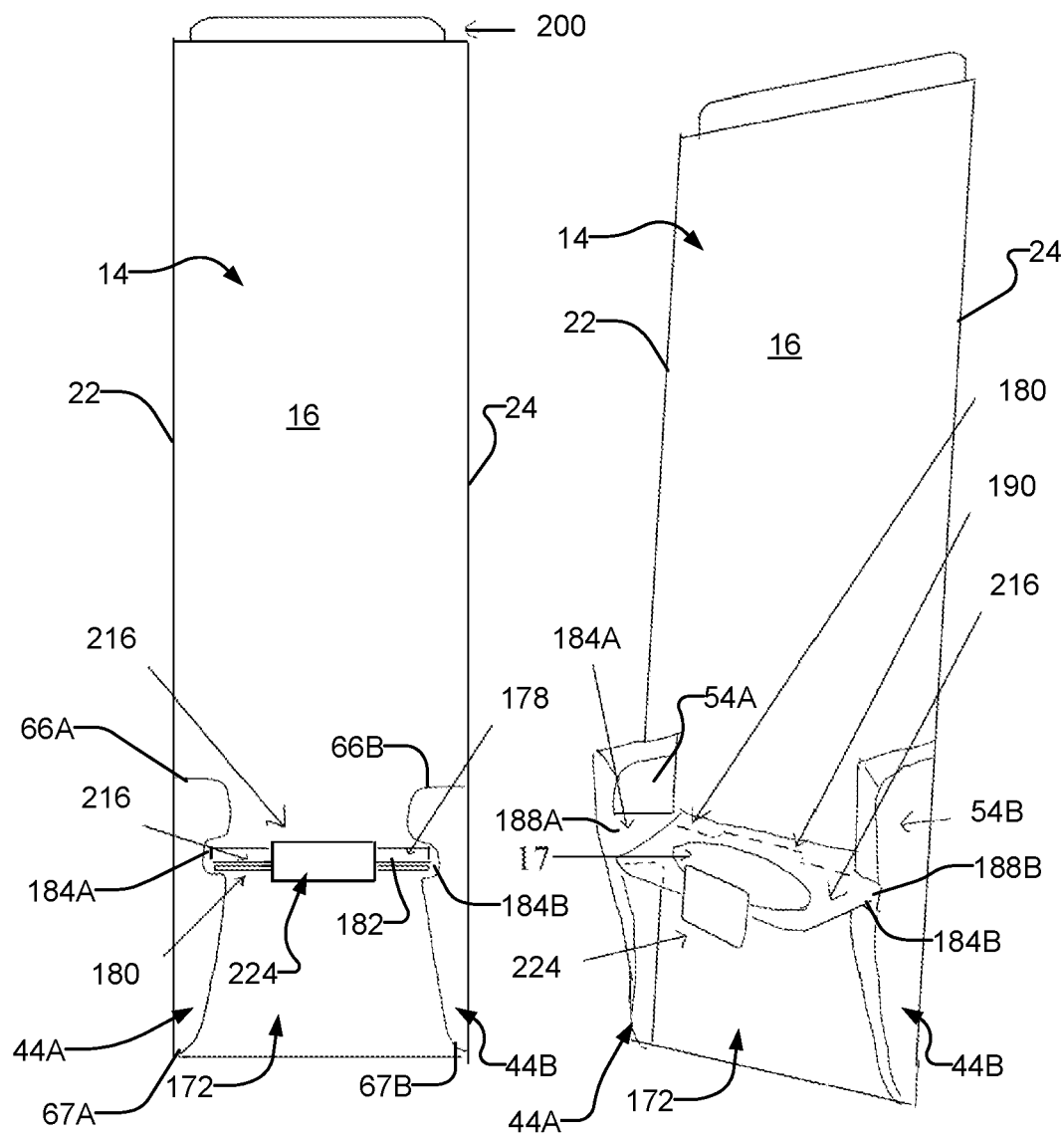
FIG. 14A is a front elevation view of the FIG. 13A embodiment.
FIG. 14B is a perspective view of the FIG. 13A embodiment.
Figure 15:
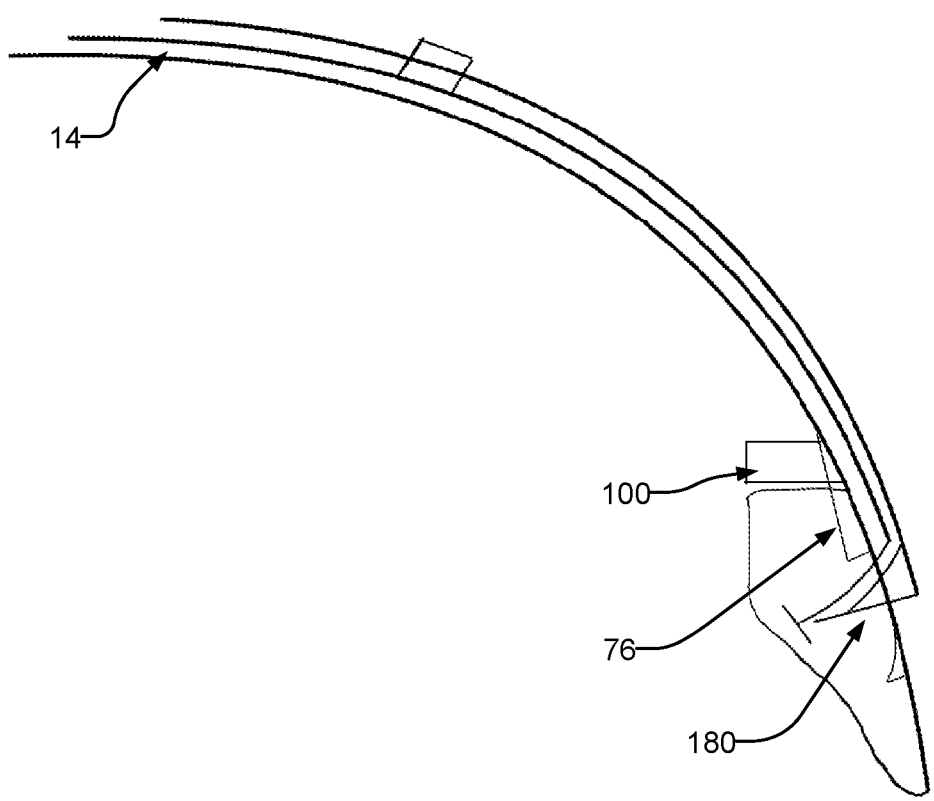
FIG. 15 is a side elevation view of an airway device according to another embodiment of the invention.
Figure 16:
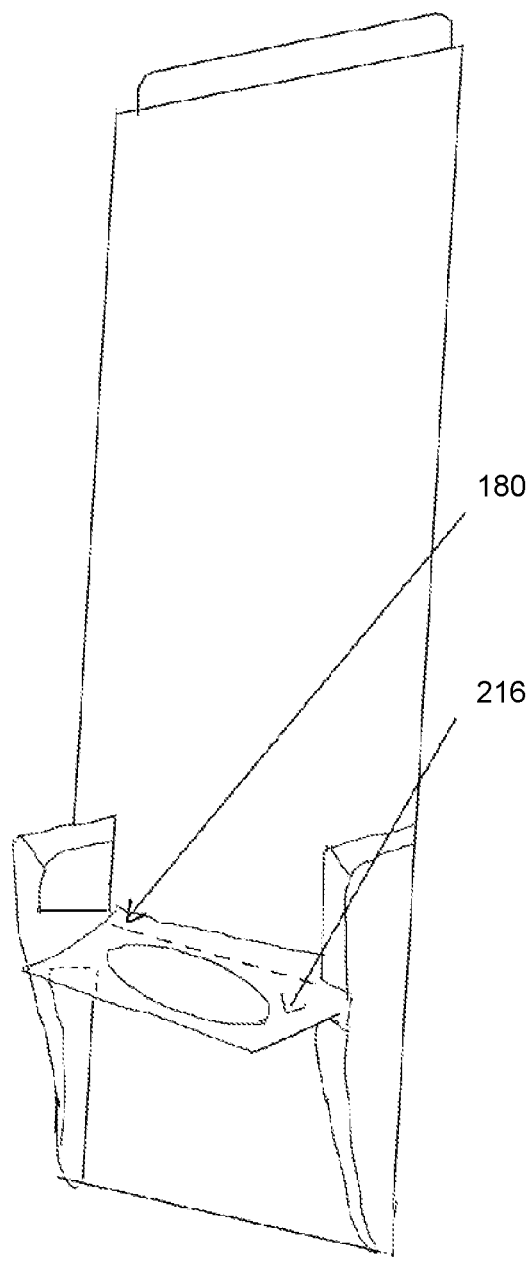
FIG. 16 is a front perspective view of an airway device according to another embodiment of the invention.

Means may be arranged to move the roll-down blade 200 along the longitudinal axis of the blade 14 within the rail 162, between a rest position (as shown in FIG. 13A) and an extended position (as shown in FIG. 13B). The distal sliding portion 216 is guided by the guide 190 and/or the base guiding plate 180 as the distal sliding portion 216 is extended distally through the elongated slot 178. The guide 190 and/or the base guiding plate 180 may serve to facilitate movement of the roll-down blade 200 from the rest position to the extended position. In some embodiments, such means comprises mechanical means, such as a knob 228 arranged to project from a first face 232A of the roll-down blade 200. In some embodiments, activating the knob 228 (e.g., by pushing the knob 228 downwardly towards base guiding plate 180) moves the roll-down blade 200 distally along a longitudinal axis of the blade 14. This moves the distal sliding portion 216 of the roll-down blade 200 forwardly through the elongated slot 178 in a direction away from the first face 16 of the blade 14. Non-limiting examples of knobs are shown in FIGS. 18A, 18B, 19A and 19B; however, any other suitable knobs may be used. In other embodiments, such roll-down blade moving means comprises electrical means. It is understood that means need not be provided to move the roll-down blade 200. The roll-down blade 200 may be moved by pressing the blade 200 down and/or moving the blade 200 at the desired direction by the operator.

Referring best to FIG. 20, in some embodiments, a roll-down blade proximal channel 234 is defined on the roll-down blade 200, which extends from the proximal lateral side 212A distally towards a point 235 along the longitudinal axis of the blade 200 between the proximal and distal lateral sides 212A,B. The roll-down blade proximal channel 234 may be dimensioned for the knob 228 to be inserted and slideable therein.

Referring best to FIGS. 13A and 13B, when the roll-down blade 200 is in the rest position, the distal sliding portion 216 of the roll-down blade 200 is arranged on the base guiding plate 180, as a result, the distal sliding portion 216 pushes downwardly on the base guide plate 180. This downward pressure causes the base guide plate 180 to be oriented at a first angle with respect to a second opposing face 232B of the roll-down blade 200 (see FIG. 13A). Referring to FIG. 13B, when the roll-down blade 200 is in the extended position, the distal sliding portion 216 is moved forwardly in a direction away from the first face 16 of the blade 14. In such embodiments, the base guide plate 180 is arranged to be oriented at a second angle with respect to a second opposing face 232B of the roll-down blade 200. In some embodiments, the first angle is greater than the second angle, such that in the rest position, the base guide plate 180 extends at a greater downward slope relative to the second face 232B of the roll-down blade 200 than in the extended position. Guided by the base guide plate 180, the distal sliding portion 216 thus extends at a greater downward slope relative to the second face 232B of the roll-down blade 200 in the rest position than in the extended position. In the rest position, a distal edge 225 of the distal plate 224 may be oriented closer to the first face 16 of the blade 14 than a proximal edge 226 thereof. Such orientation may facilitate passing of the distal region 40 of the blade 14 from the back of the epiglottis, particularly when the space between the tip of the epiglottis and the back wall of the throat is small. In some embodiments, in the extended position, the sliding distal portion 216 is oriented substantially horizontal or orthogonal to the second face 232B of the roll-down blade 200. The distal plate 224, if present, may be oriented substantially vertical or orthogonal to the sliding distal portion 216 when the roll-down blade 200 is in the extended position. Such orientation may facilitate transmitting a suitable force to the epiglottis forwardly, and/or facilitate creating a passageway for the ETT.

Means may optionally be provided to move the distal plate 224 and/or the distal sliding portion 216 of the roll-down blade 200 to a desired position within the oropharyngeal cavity. Any suitable means may be provided including for example mechanical means (e.g., gears, telescoping cylinders, hydraulic systems, pneumatic systems, etc.) and/or electrical means. In one non-limiting example embodiment, one or more struts are arranged on a back side of the distal plate 224 (e.g., at a side facing the distal tip 70 of the blade 14 when the distal sliding portion 216 is extended out of the elongated slot 178) at a first end, and to the rail 162 at an opposing second end. One or more wires may be connected directly or indirectly (e.g., via hooks or similar attachment means) to the back side of the distal plate 224. In the resting position, the one or more wires may be pulled upwardly, thereby compressing the struts, and the distal plate 224 is positioned proximate to the blade 14 and the base guiding plate 180. Upon releasing the one or more wires, the struts expand and the distal sliding portion 216 is moved forwardly, thereby displacing the epiglottis forwardly at the desired position within the oropharyngeal cavity.

Figure 24:
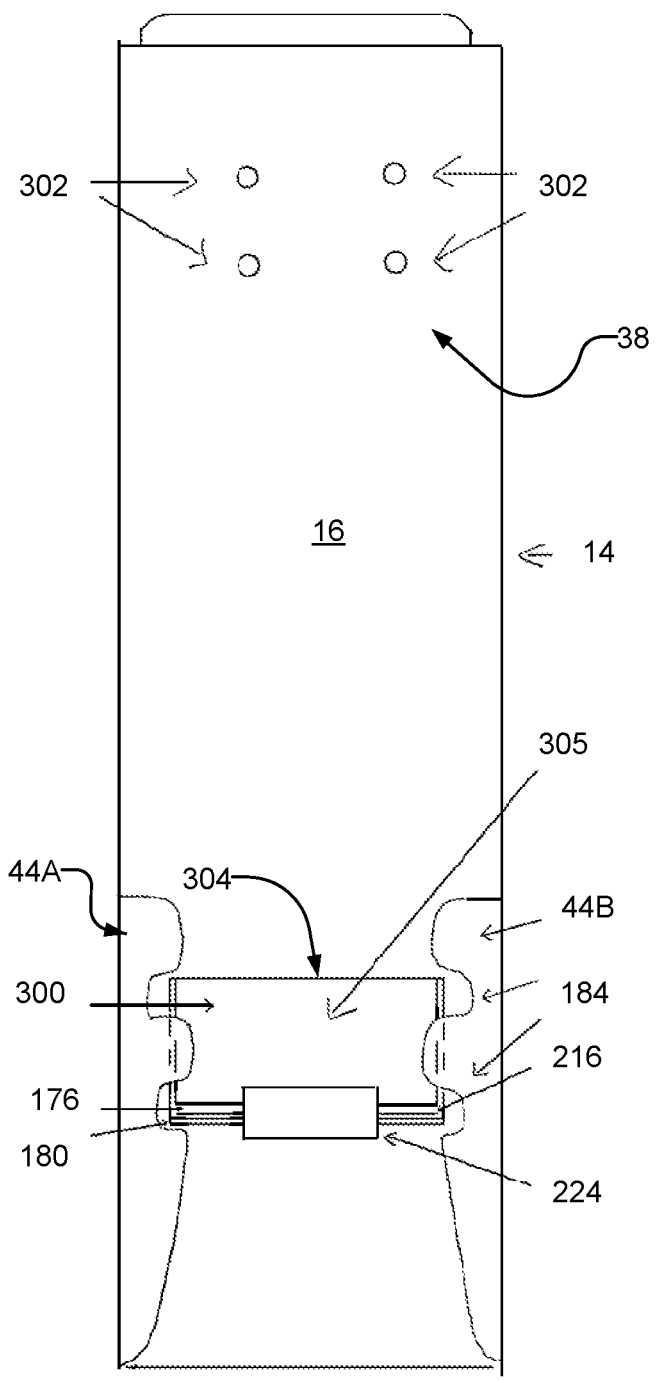
FIG. 24 is a front elevation view of an airway device according to another example embodiment of the invention.

One or more additional blades may be arranged with the blade 14 and/or the roll-down blade 200. In some embodiments, the one or more additional blades are received within the rail 162 for movement therein. The one or more additional blades may be positioned in front of or at a back of the roll-down blade 200. In some example embodiments, a posterior blade is positioned at the back of the roll-down blade 200, and an anterior blade is positioned in front of the roll-down blade 200, such that the roll-down blade 200 is sandwiched between the posterior and anterior blades within the rail 162 with the anterior blade being oriented most proximate to the blade 14. In some embodiments, the additional blade(s) may be arranged to move the base guiding plate 180 at a desired position (e.g., upwardly or downwardly) based on the subject's anatomy and/or his/her/its location of the epiglottis. FIG. 24 illustrates one non-limiting example embodiment. As shown in the illustrated embodiment, the one or more additional blades comprises an anterior blade 300. The anterior blade 300 may comprise an elongated rectangular shape similar to the roll-down blade 200, but may have a width and/or length greater or less than the roll-down blade 200. The anterior blade 300 may comprise one or more pins 302. In such embodiments, the blade 14 may comprise one or more holes defined therein, for receiving the one or more pins 302 of the anterior blade 300. The one or more holes may be positioned at the proximal region 38 of the blade 14. The pins 302 of the anterior blade 300 may engage the holes of the blade 14 at the first face 16 of the blade 14, and/or the second face 17 thereof. A distal portion 304 of the anterior blade 300 may be arranged to project out of a blade slot 305 arranged proximal to the elongated slot 178, with the distal sliding portion 216 of the roll-down blade 200 being positioned at the back of the distal portion 304 of the anterior blade 300, in front of the distal portion of the posterior blade. The distal portion of the posterior blade may in such embodiments serve the function as the base guiding plate 180. The one or more additional blades may comprise optional features such as a distal conduit having a channel dimensioned for the roll-down blade 200 to pass therethrough and/or clefts 184 and/or ramps and the like at the distal portion 304 of the one or more additional blades to provide similar or substantially the same functions as the base guiding plate 180.

Figure 25:
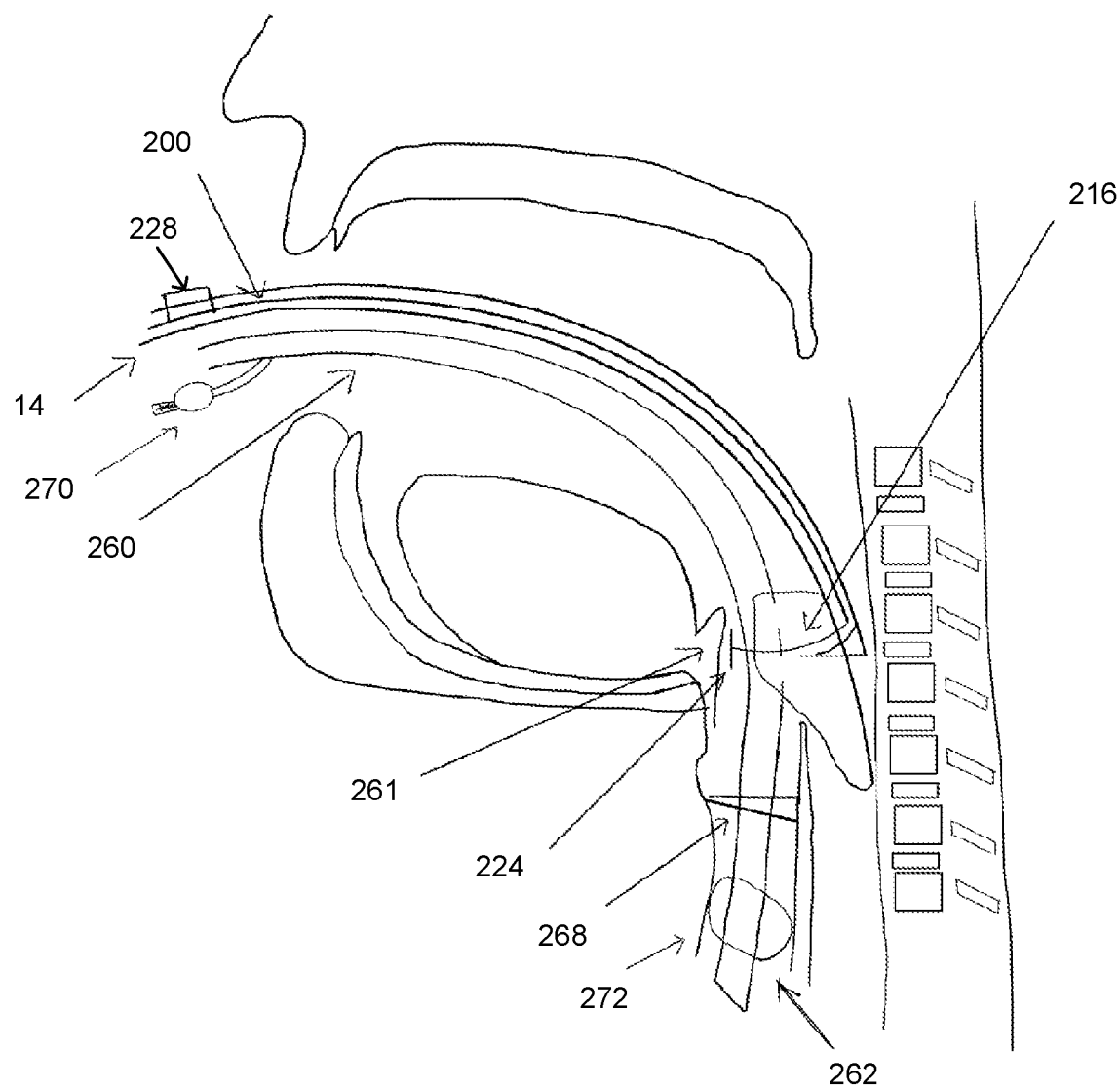
FIG. 25 is a schematic diagram illustrating an ETT arranged on an airway device advanced into the oropharyngeal cavity according to an example embodiment of the invention.

An example method of use of the FIGS. 13-24 embodiment is as follows. The device 10 is inserted into a mouth of a subject and placed in the desired position within the oropharyngeal cavity as described with respect to the method of using the FIG. 1-11 embodiment of the invention. The schematic diagram in FIG. 25 shows the device 10 being at the desired position within the oropharyngeal cavity. At such desired position, the sliding distal portion 216 and the distal plate 224 of the roll-down blade 200 are moved forwardly (or outwardly through the elongated slot 178) by pushing the knob 228 downwardly and placing it between the markers on the rails, thereby moving the epiglottis 261 forwardly. The ETT 260 may then be arranged to pass through the central passage 220 of the sliding distal portion 216 and extends forwardly, thereby passing through the vocal cords 268 and is placed inside the trachea 272. Once the ETT 260 is inside the trachea 272, the cuff 262 of the ETT 260 may be inflated by the ETT pilot bladder 270. In some embodiments, one or more stylets (with or without moveable tips), introducers, and/or special ETTs with a centrally placed tip or pressing on the cricoid or thyroid cartilage may be used in conjunction with the device 10 to facilitate passage of the ETT through the central passage 220 and vocal cords 268.

One or more added features and/or accessories may be provided and/or connected to the blade 14 to improve the functionality of the airway device 10.

In some embodiments, one or more tubes 250 may be arranged along the blade 14. FIG. 11 illustrates one non-limiting example placement of such tubes 250 with respect to the blade 14. As illustrated, the tube 250 may extend proximally along the longitudinal axis of the blade 14, from a distal end 252A arranged on the distal plate region 72 of the blade 14, and extend to pass through or adjacent to one of the side components 44A,B and therefrom continues to extend along one of the first and second longitudinal edges 22, 24 of the blade 14, towards a proximal end 252B thereof. The distal end 252A may in some embodiments be positioned along a central longitudinal axis of the blade 14. The one or more tubes 250 may for example be used as a drainage tube. The one or more tubes 250 may also be used for the passage of a nasogastric tube extending from the mouth into the stomach of a subject. In some embodiments, the proximal end 252B of the tube 250 is attachable to a suction device, adapted for removing secretions, regurgitated food, blood, or other materials that may be present in the laryngopharynx and/or upper esophagus so as to prevent pulmonary aspiration and/or to facilitate intubation. One or more side holes 254 may optionally be defined on the tube 250, for example near the distal end 252A thereof. The one or more side holes 254 may be arranged facilitate the removal of materials. The one or more tubes 250 may extend along any suitable one or more of the sides and/or face of the blade 14.

One or more inflatable balloons may be arranged along one or more of an edge, and/or side and/or surface of the blade 14 and/or the roll-down blade 200. For example, in the FIG. 22 embodiment, an inflatable balloon 280 is arranged at one or both edges of the distal lateral side 212B. In such embodiments, a delivery tube 284 is arranged to extend proximally from an entry point 281 which is joined to the inflatable balloon 280 along one of the longitudinal sides 208A,B of the roll-down blade 200 to the proximal lateral side 212A of the roll-down blade 200. A pilot bladder 288 may be connected to the delivery tube 284, adapted to inflate the inflatable balloon 280 at a desired stage of advancement, e.g., once the roll-down blade 200 extends forwardly through the elongated slot 178 of the blade 14.

Figure 23:
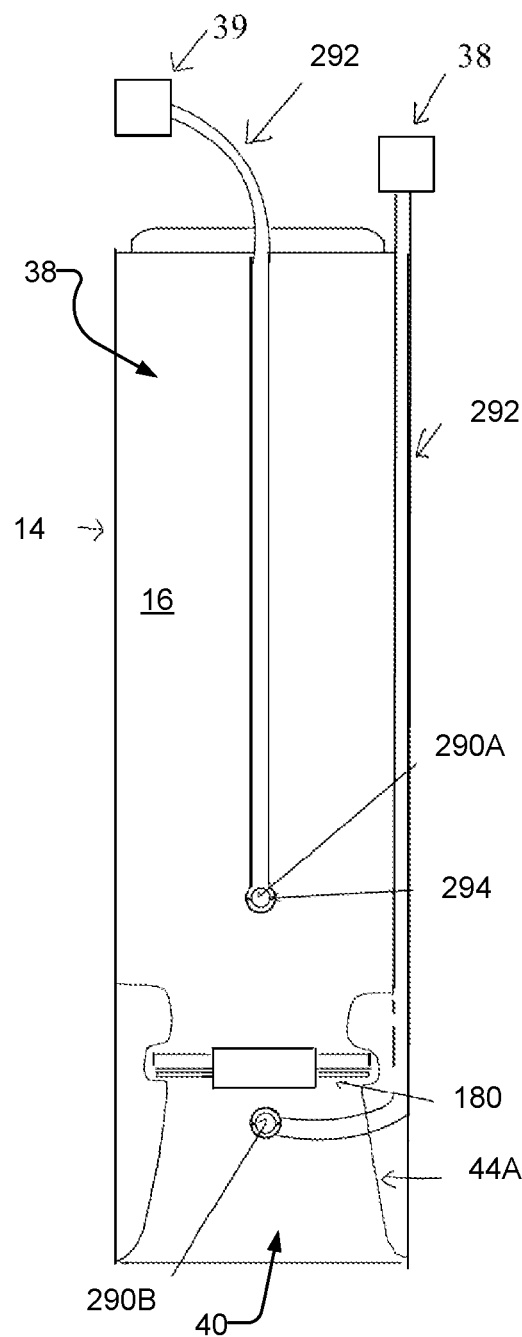
FIG. 23 is a front elevation view of an airway device according to another example embodiment of the invention.

One or more cameras may be securable to the blade 14, arranged to perform visualized intubation. The one or more cameras may be provided to visualize the laryngeal structures in difficult or compromised airways compared to video laryngoscopy, and may provide an improved view for use in combination with Total Control Introducer™ and other introducers. The one or more cameras may be positioned at any suitable positions along the blade 14. FIG. 23 shows one non-limiting example of possible placement of the one or more cameras. In the illustrated embodiment, the one or more cameras comprises a proximal camera 290A arranged at the proximal region 38 of the blade 14, and a distal camera 290B arranged at the distal region 40 of the blade 14. The proximal camera 290A may for example be arranged to be positioned at a central longitudinal axis of the blade 14. The distal camera 290B may for example be positioned at a central longitudinal axis of the blade 14, distal to the base guiding plate 180 and/or the ramp 76 (if present). The cameras 290A,B may each be exposed through a hole defined on the blade 14. The cameras 290A,B may be connected to external devices (e.g., monitors, processors (e.g., mobile devices such as cell phones tablets, computers), wireless transceivers (e.g., Bluetooth and WiFi), etc.) with or without cables 292 which may each be secured to the camera 290A,B at one end, and extend proximally beyond the proximal lateral edge 26 of the blade 14 to secure the such external devices at an opposite end thereof. The cables 292 may extend on a first or second face 16.17 of the blade 14, or along a lateral 26,30 and/or longitudinal edge 22,24 thereof. In some embodiments, the cameras 290A,B need not be connected to cables 292. One or more of the cameras 290A,B may be wirelessly communicatively connected to the external devices. In some embodiments, one or more lights 294 are arranged to surround the cameras 290A,B. In some embodiments, one or more holders may be arranged to secure the cables 292 in position. The one or more holders may for example comprise a hollow tube or an incomplete hollow tube. In some embodiments, the edges of the blade 14 which define the hole for insertion of the camera 290A,B may be inclined, arranged downwardly sloping from the second face 17 to the first face 16 of the blade 14. In some embodiments, the edges of the blade 14 which define the hole for insertion of the camera 290A,B may protrude outwardly to create an extended hole, so as to provide a greater depth. In some example embodiments, an elongated camera blade may be arranged to be secured to a first and/or second face 16,17 of the blade 14. The elongated camera blade may comprise holes configured for receiving a camera, and optionally one or more holders for stabilizing the cameras. The elongated camera blade may be arranged for vertical displacement along a longitudinal axis of the blade 14, so that the one or more cameras may be vertically displaced, so as to improve visual information from the proximal structures of the laryngopharynx. The elongated camera blade for example may be securable to the blade 14 by one or more pins. In some embodiments, the elongated camera blade is securable to the second face 17 of the blade 14, and in some embodiments, between the first and second longitudinal rail arms 166,168 of the rail 162.

Figure 26A:
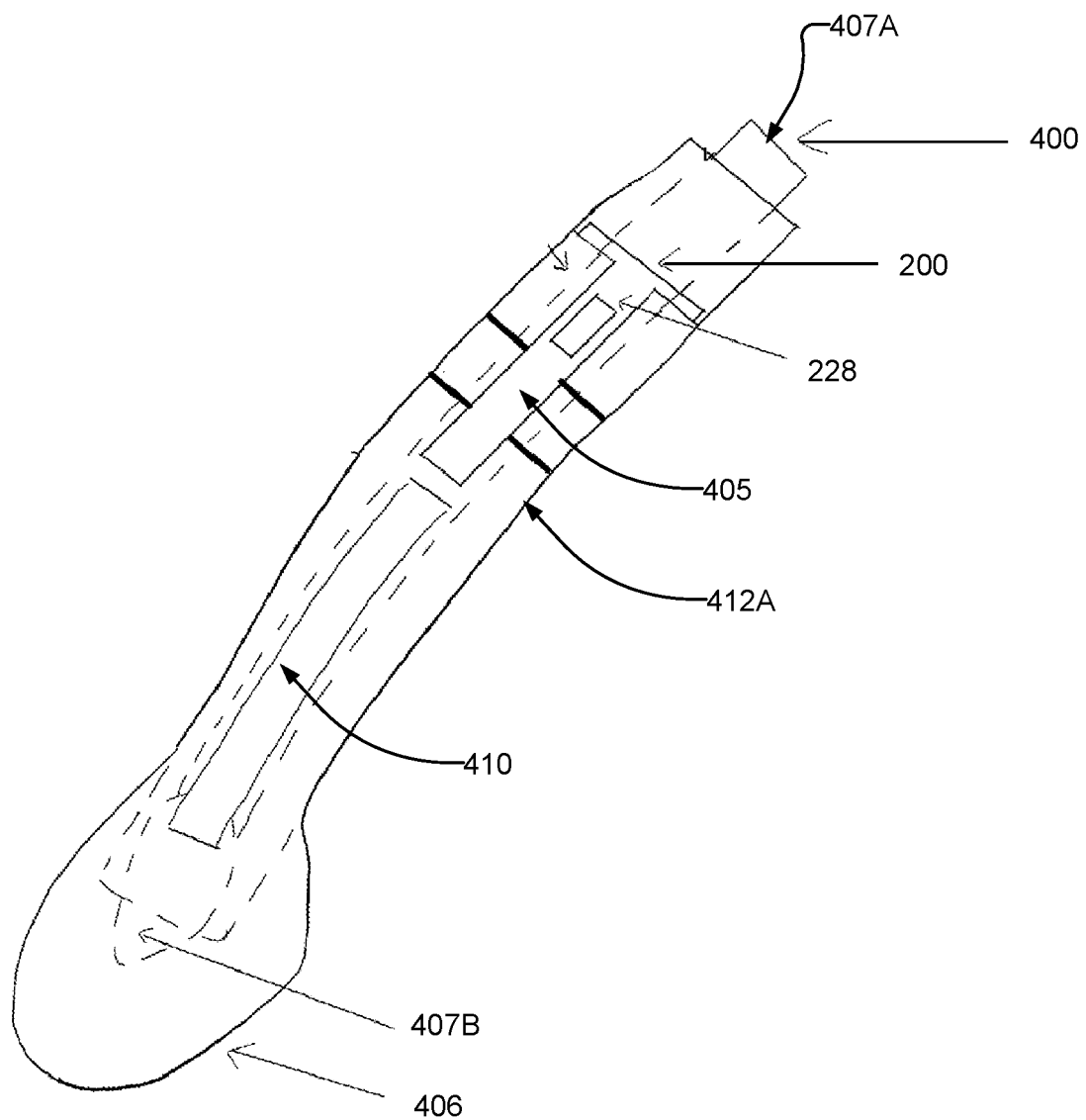
FIG. 26A is a perspective view of an airway device according to another example embodiment.
Figure 26B:
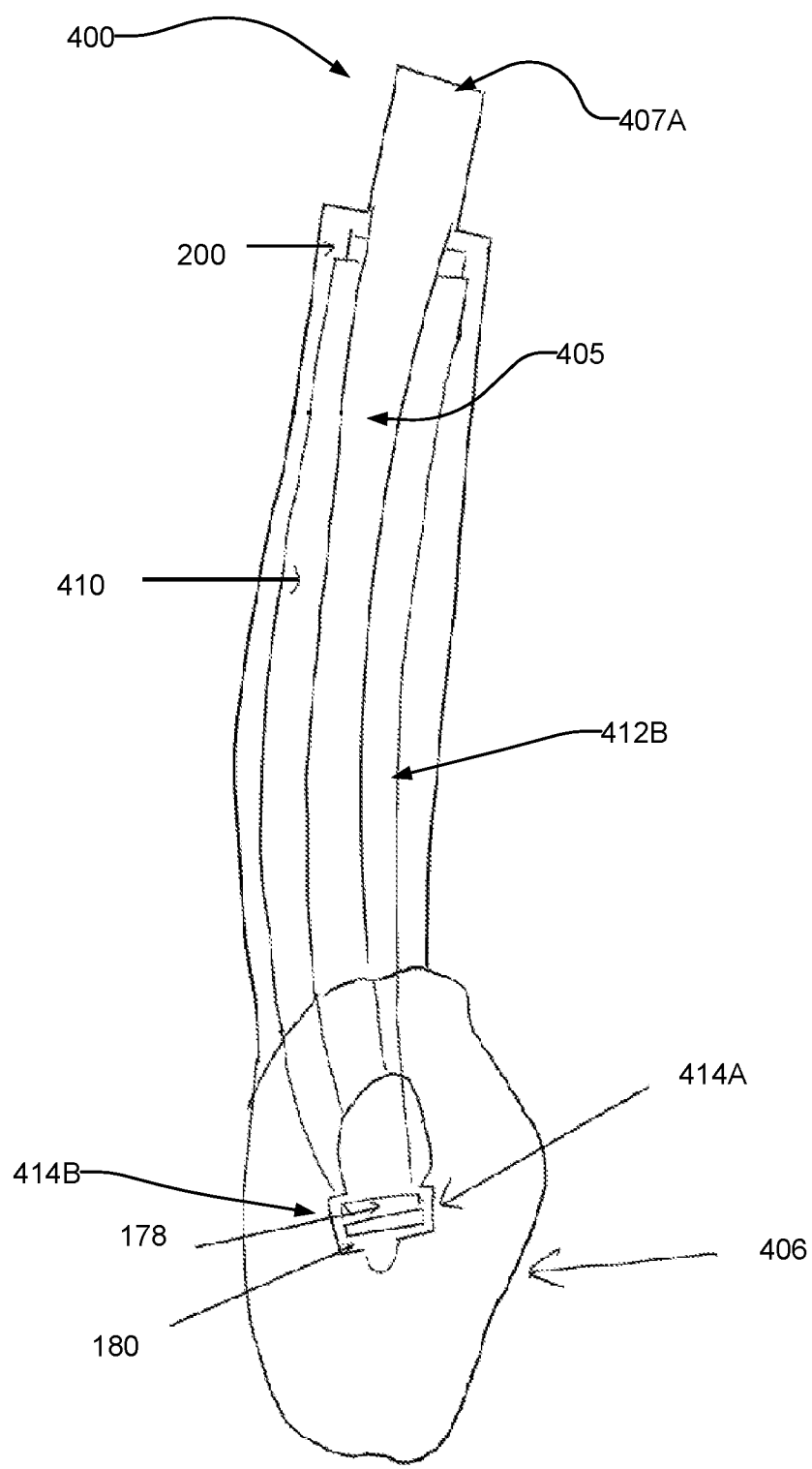
FIG. 26B is a front perspective view of the FIG. 26A airway device.

In some embodiments, the device 10 is combined with a second airway device such as an i-Gel™ or a similar device, for use to advance the epiglottis and/or create a central passage for endotracheal intubation. Referring to FIGS. 26A and 26B, the second airway device 400 may comprise a proximal end extending along an elongated tube 405 from a proximal end 407A of the elongated tube 405 to an opposing distal end 407B. A parapharyngeal bowl 406, which may be inflatable or non-inflatable, may surround the opposing distal end 407B of the elongated tube 405. A rail 410 may be arranged along the elongated tube 405, adapted to receive therein the blade 14 and/or the roll-down blade 200 and which may be slideable therein. The rail 410 may comprise a similar configuration as the rail 162. In some embodiments, the knob 228 of the roll-down blade 200 projects outwardly from a back side 412A of the elongated tube 405 between longitudinal rail arms. In some embodiments, the roll-down blade 200 is slideable within the rail 410. The elongated slot 178 and the base guiding plate 180 of the blade 14 may for example be arranged at the distal end 407B of the elongated tube 405. In some embodiments, a pair of bowl clefts 414A,B may be defined on opposing inner side walls of the parapharyngeal bowl 406. The bowl clefts 414A,B may be arranged at or near the lateral opposing sides of the elongated slot 178 and/or the base guiding plate 180. In such embodiments, the pair of side components 44A,B may be omitted. In such embodiments, the distal sliding portion 216 of the roll-down blade 200 may pass forwardly through the elongated slot 178 of the blade 14. The opposing lateral sides of the distal sliding portion 216 may be surrounded by the bowl clefts 414A,B. The bowl clefts 414 may facilitate changing of the direction of the movement of the distal sliding portion 216 (e.g., from a vertical plane to a horizontal plane relative to the face of the blade 14), so that the distal sliding portion 216 may press the epiglottis forwardly and create a passageway for ventilating the patient, and/or allow passage of the ETT towards the vocal cords and into the trachea.

In some example use embodiments, after the device 10 and the airway device 400 are placed within the desired position within the oropharyngeal cavity, an endotracheal tube may be passed through the proximal end 407A of the elongated tube 405 and through the central passage 220 and be arranged above and/or below the vocal cords. In some other embodiments, the proximal end 407A of the elongated tube 405 may be attached to a ventilatory support means for providing supraglottic ventilation before or after advancing the sliding distal portion 216. The proximal end 407A optionally comprises a connector for coupling to such means.

Modifications to the second airway device may be made to improve functionality and/or usability of the device 10. For example, the dimensions and/or shape and/or physical properties of the parapharyngeal bowl 406 may be adjusted to prevent downfolding of the epiglottis. For example, the thickness of the distal tip of the parapharyngeal bowl 406 may be less than the thickness of the other regions of the bowl 406. In another example, an epiglottis rest may be arranged to protrude outwardly from a proximal region of the parapharyngeal bowl 406. In some embodiments, a cover may be arranged along a portion or an entire length of the elongated tube 405 at one or both of the front and back sides 412A,B thereof. The cover may for example serve as a bite blocker, to prevent the blade 14 and/or roll-down blade 200 from being bitten by the subject during advancement of the device 10.

The illustrated embodiments are examples of how the added features and/or accessories may be connected, joined or otherwise included for use with certain embodiments of the invention. It would be understood that such added features and/or accessories may be used in conjunction with any embodiments of the invention as discussed herein.

Figure 27:
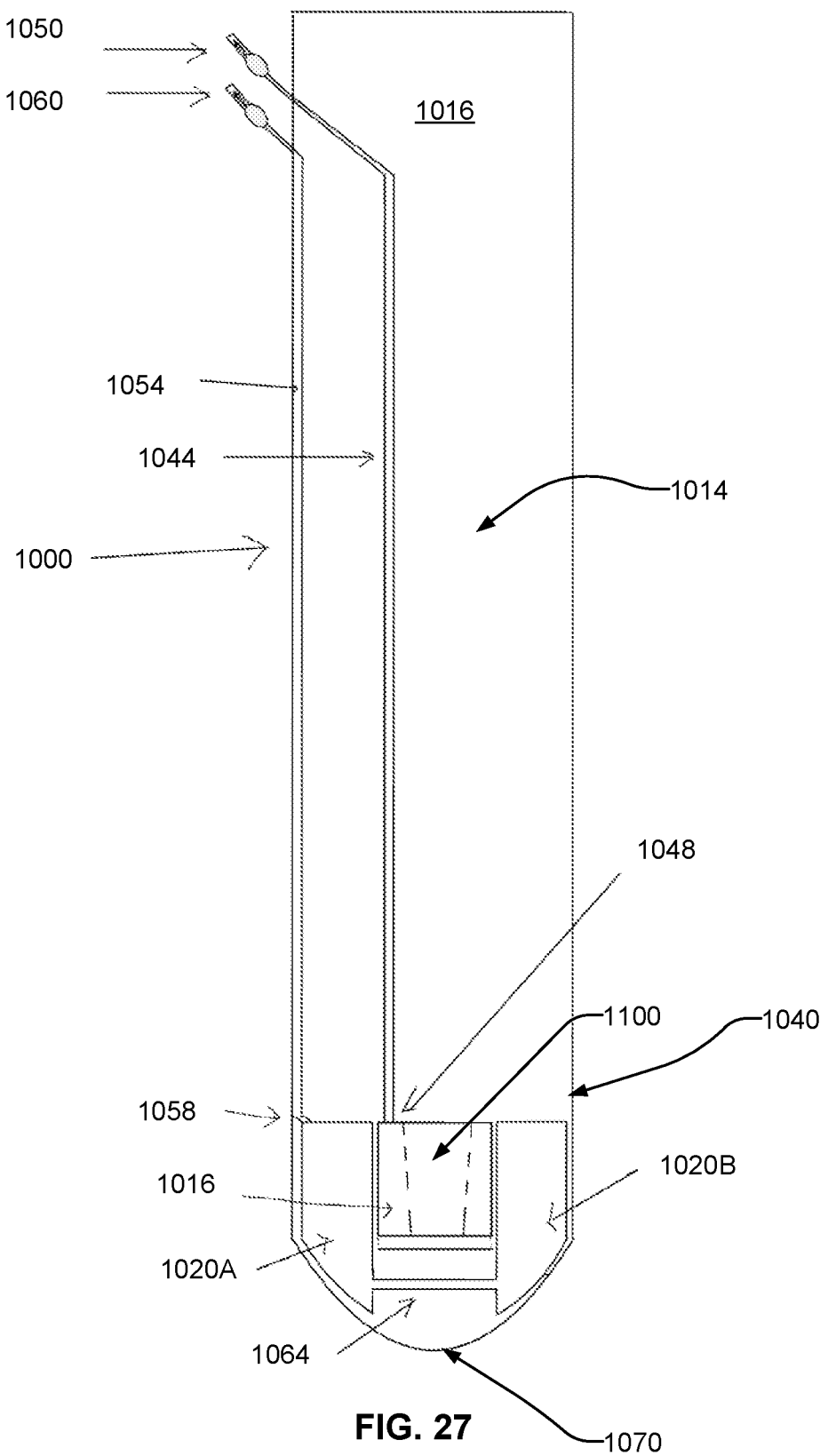
FIG. 27 is a front elevation view of an airway device according to another embodiment of the invention.
Figure 28:
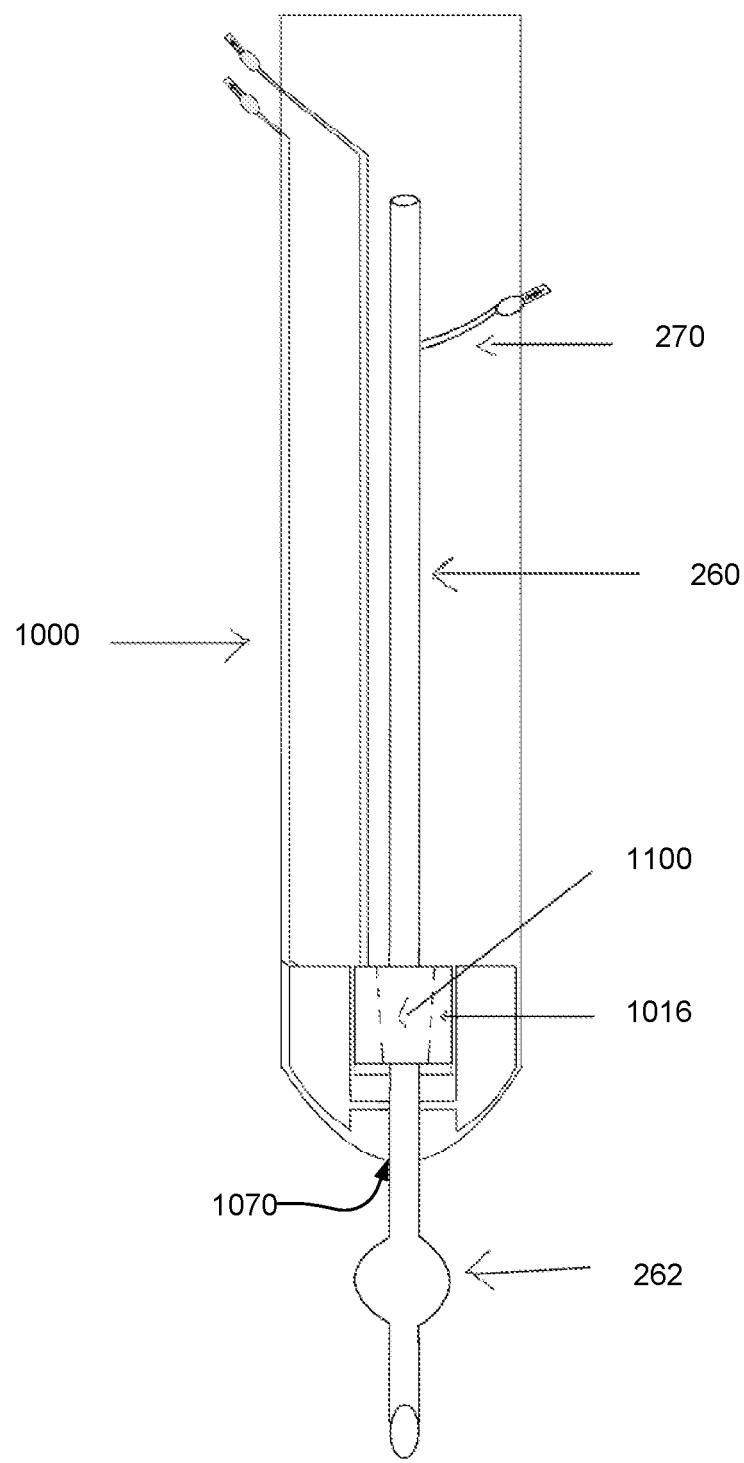
FIG. 28 is a front elevation view of the FIG. 27 airway device with an ETT advanced thereon.
Figure 29A:
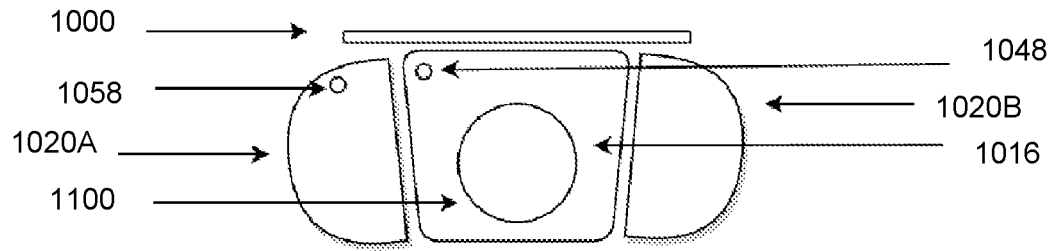
FIG. 29A is a top elevation view illustrating the central bladder and the side bladders according to an example embodiment of the invention.
Figure 29B:
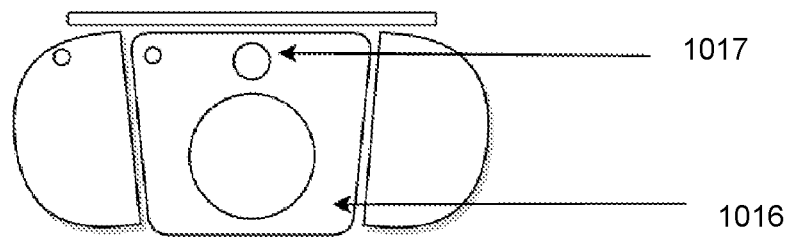
FIG. 29B is a top elevation view illustrating the central bladder and the side bladders according to another example embodiment of the invention.
Figure 29C:
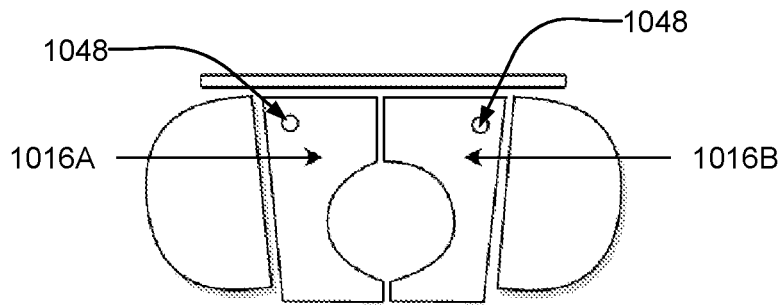
FIG. 29C is a top elevation view illustrating the central bladder and the side bladders according to another example embodiment of the invention.
Figure 29D:
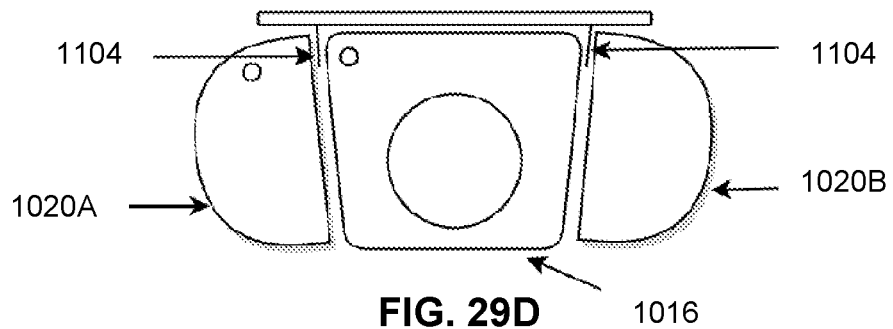
FIG. 29D is a top elevation view illustrating the central bladder and the side bladders according to another example embodiment of the invention.

Other non-limiting examples of added features and/or accessories that may be provided and/or connected to the blade 14 at any suitable position along the blade 14 include:

a handle securable to the proximal region 38 of the blade 14; and/or one or more mirrors (e.g., flexible mirrors) arranged on the first face 16 of the blade 14; and/or depth markers arranged on the first and/or second faces 16,17 along the blade 14 for example on the rail 162; etc, FIGS. 27-29 illustrate an airway device 1000 according to another embodiment of the invention. The airway device 1000 comprises a blade 1014 having an elongated body similar to the configuration of the blade 14. In some embodiments, the airway device 1000 comprises a central bladder 1016 and a pair of side bladders 1020A,B arranged at each opposing sides of the central bladder 1016 along a lateral axis of the blade 1014. The central bladder 1016 and the side bladders 1020A,B may be arranged at a distal region 1040 of the blade 1014. In some embodiments, one or both of the central bladder 1016 and the side bladders 1020A,B are inflatable. Inflating the central bladders 1016 may facilitate forward displacement of the epiglottis when the device 10 is in place. In some embodiments, one or both of the central bladder 1016 and the side bladders 1020A,B are not inflatable. In such embodiments, the one or both of the central bladder 1016 and the side bladders 1020A,B may be formed of any suitable pliable or gel-like material or combination of materials, including but not limited to silicone, thermoplastic polyurethane, thermoplastic elastomers such as styrene ethylene butadiene styrene, or any other types of polyurethane, polyethylene, and medically compatible polymeric materials.

A central delivery tube 1044 may be arranged to connect the central bladder 1016 at a central entry point 1048 thereof to a central pilot cuff 1050, arranged to inflate the central bladder 1016. One or more side delivery tubes 1054 may be arranged to connect the side bladders 1020A,B at one or more side entry points 1058 thereof to one or more side pilot cuffs 1060, arranged to inflate the side bladders 1020A,B. In some embodiments, one side delivery tube 1054 is arranged to connect the side bladders 1020A,B at one side entry point 1058 to the side pilot cuff 1060. In such embodiments, a side bridge tube 1064 may be arranged to attach the two side bladders 1020A,B. For example, the central pilot cuff 1050 and/or the side pilot cuffs 1060 may comprise spring-loaded one-way valves adapted to inflate the respective bladders. The delivery tubes 1044, 1054 may be arranged to extend proximally in a direction opposite to the distal tip 1070 of the blade 1014 along the longitudinal axis of the blade 1014, along the first face 1016 of the blade 1014. The bladders may however be inflated by any other suitable means, including but not limited to pneumatic and/or electrical sources.

In some embodiments, a central passage 1100 may be defined within the central bladder 1016. An ETT 260 may be arranged to pass therethrough in the direction towards the distal tip 1070 of the blade 1014. In some embodiment, a diameter of the central passage 1100 decreases from a proximal end to a distal end thereof.

FIGS. 29A-29D are top elevation views of the central bladder 1016 and the side bladders 1020A,B according to non-limiting example embodiments. In some embodiments, the central bladder 1016 has the central passage 1100 and the central entry point 1048 defined therein, and one side entry point 1058 defined in one of the side bladders 1020A (see FIG. 29A). In some embodiments, an additional one or more passages 1017 may be defined within the central bladder 1016 arranged to pass other devices therethrough, for example a nasogastric tube (NG) or the like (see FIG. 29B). The central bladder 1016 may in some embodiments be formed of two or more portions, 1016A, 1016B. The two or more portions may be shaped to define the central passage 1100. In such embodiments, two central entry points 1048 may be arranged on each portion of the central bladder 1016. In some embodiments, a cleft may be defined on the central bladder 1016, extending from a distal edge towards the central passage 1100 (see FIG. 29C). The cleft may assist with removing the ETT from the central bladder 1016. In some embodiments, one or more limiting plates 1104 may be arranged between bladders 1016, 1020A,B or on the surface (s) and/or sides of the bladders 1016, 1020A,B, arranged to limit the movement of the respective bladders (see FIG. 29D). In some embodiments, means are provided to adhere the bladders 1016, 1020A,B with one another. Such means may for example comprise magnets but other suitable fastening and/or attachment means may alternatively be used.

In some embodiments, portions of the proximal region of the blade 1014 is replaced by a tube. In such embodiments, the tube may extend proximal to the distal region 1040 of the blade 1014 which comprises the bladders 1016, 1020A,B. In some embodiments, the tube extends distally from a proximal end and terminates adjacent to a proximal lateral edge of the bladders 1016, 1020A,B. The tube may for example provide a pathway for the ETT. Alternatively, the tube may be attached to ventilation means without passing the ETT, which may function as a supraglottic airway for maintaining the airway and providing low-pressure ventilation.

In some embodiments, the blade 1014 extends along one or more curved regions between opposing lateral edges. In some example embodiments, the blade 1014 extends from a proximal end and extends to a downward curved region and therefrom extends to an upward curved region, and terminates at a distal end. A downward curved region may refer to a direction towards a surface on which the blade 1014 is placed on, and an upward curved region may refer to a direction opposite to the downward direction, in a direction towards the atmosphere. A curved blade may facilitate attachment of the blade to the back wall of the throat of a subject in the event that the side bladders 1020A,B cannot be sufficiently inflated to perform this function when the blade passes the uvula.

Any suitable components described in the FIGS. 1-11 and 13-24 embodiments above may be included in the FIGS. 27-29 embodiments. These include but are not limited to one or more ramps (such as ramp 76), epiglottis elevating bar 120, proximal and/or distal conduits 100, 150, etc. Such components may for example replace and/or substitute certain components described in FIGS. 27-29 where suitable. For example, in some embodiments, the central bladder 1016 may be replaced with a ramp 76 alone, or a ramp 76 with an epiglottis elevating bar 120, arranged between the pair of side bladders 1020A,B. As another example, in some embodiments, the side bladders 1020A,B may be replaced by the side components 44, positioned at opposing lateral sides of the central bladder 1016. In some example embodiments, the central bladder 1016 (and the accompanying central delivery tube 1044 and accessories) and/or the epiglottis elevating bar 120 may be used to replace the roll-down blade 200 in the FIG. 26A, 26B embodiment.

Figure 30A:
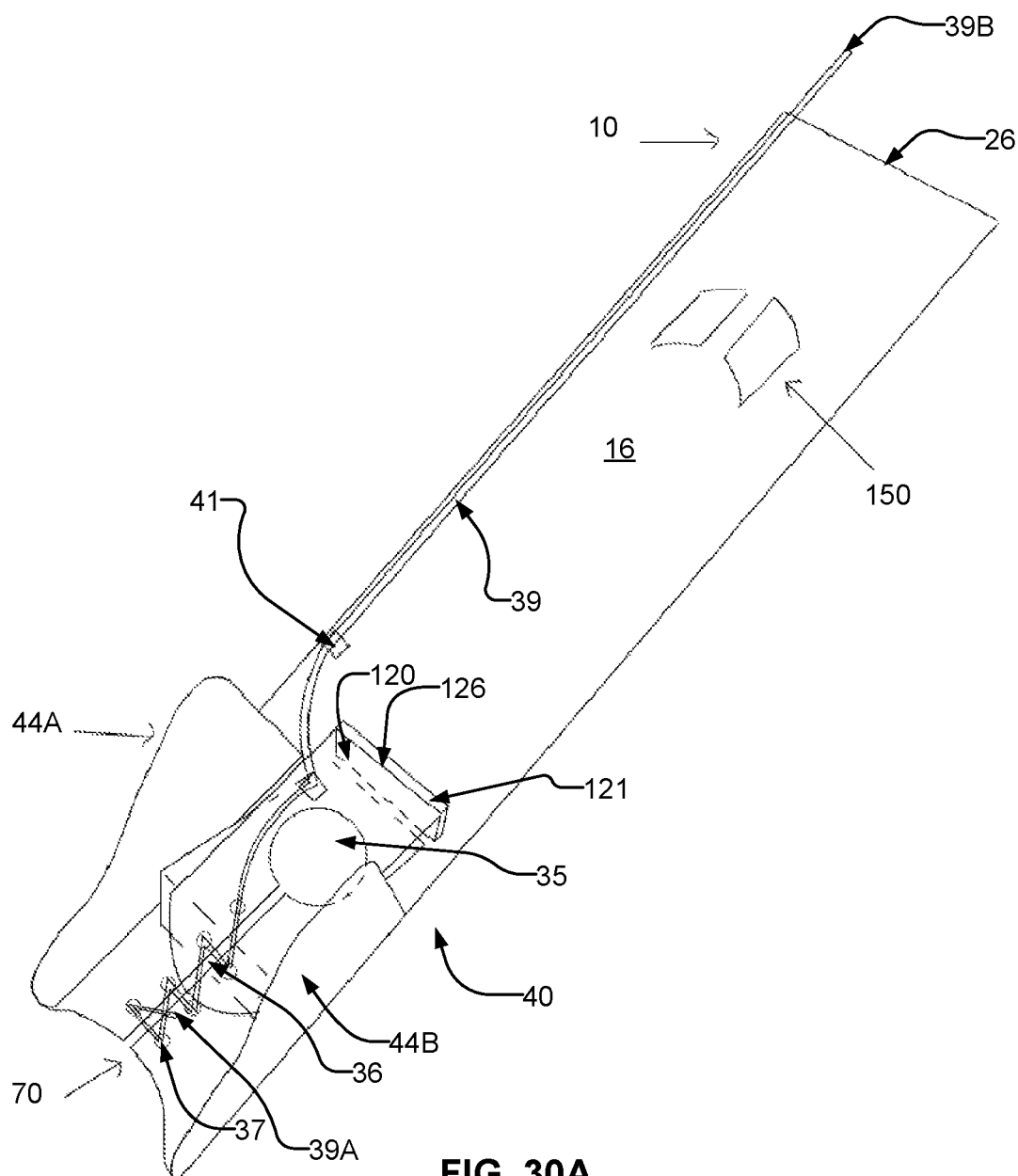
FIG. 30A is a front perspective view of an airway device according to another example embodiment of the invention.
Figure 30B:
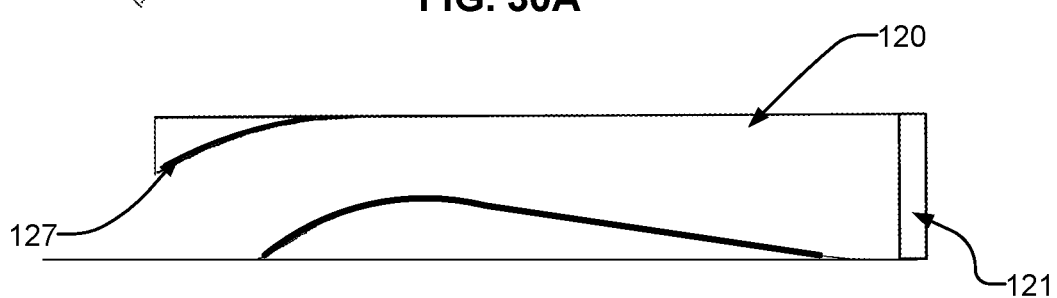
FIG. 30B is a close-up side elevation view of an epiglottis elevating bar of the FIG. 30A embodiment.

FIGS. 30A and 30B illustrate another embodiment of the invention. In such embodiments, a hole 35 is defined on the blade 14 at the distal region 40 thereof. The hole 35 may in some embodiments, be positioned between the proximal and distal lateral ramp sides 84, 88 and/or between the first and second ramp longitudinal sides 80, 83 of the ramp 76. In embodiments in which the epiglottis elevating bar 120 is present, the hole 35 may be positioned between the first and second longitudinal edges 122,124 and/or between the proximal and distal lateral edges 126,128 of the epiglottis elevating bar 120. However, it would be understood that the hole 35 may be positioned at other suitable positions along the blade 14, for example, proximal to one or both of the proximal lateral ramp side 84 of the ramp 76.

A cleft 36 may be defined on the blade 14, arranged to extend distally from the hole 35 to a point on the distal plate region 72 of the blade 14. In some embodiments, the cleft 36 extends from a point on the hole 35 most proximate to the distal tip 70 of the blade 14. The point may be along a central longitudinal axis of the blade 14. In some embodiments, the cleft 36 extends to the distal tip 70 of the blade 14. The cleft 36 may be arranged along a central longitudinal axis of the blade 14. In some embodiments, the proximal lateral edge 126 of the epiglottis elevating bar 120 is arranged proximal to the proximal lateral ramp side 84 of the ramp 76. In some embodiments, a base 121 joins the proximal lateral edge 126 of the epiglottis elevating bar 120 to the first face 16 of the blade 14. The base 121 may be arranged to project outwardly from the first face 16 of the blade 14. In some embodiments, the base 121 is oriented orthogonal to the first face 16 of the blade 14. The base 121 need not be present. In some other embodiments, the proximal lateral edge 126 of the epiglottis elevating bar 120 is joined to the first face 16 of the blade 14 directly.

A plurality of holes 37 may be arranged at opposing longitudinal sides of the cleft 36, spaced-apart along a length of the cleft 36. The plurality of holes 37 may have a diameter smaller than a diameter of the hole 35. The plurality of holes 37 are dimensioned to allow passage of a string 39 or any suitable tensioning material(s) (e.g., wire, cord and the like). The string 39 may extend proximally along a longitudinal axis of the blade 14, from a distal end 39A, arranged to pass through each of or at least some of the plurality of holes 37, to the proximal end 39B thereof. In the illustrated embodiments, the string 39 is arranged to pass through the plurality of holes 37 in a zigzag pattern but this is not necessary. The string 39 may be arranged to pass through the plurality of holes 37 in any other suitable pattern so as to pass the string 39 between the cleft 36 along the longitudinal length of the cleft 36. The distal end 39A may in some embodiments be secured by placing the end 39A underneath a more proximal part of the string 39, but other suitable securing means may be provided. The string 39 may be arranged to extend on the first face 16 of the blade 14 towards the proximal lateral edge 26 but this is not necessary. The string 39 may extend on any face 16,17 and/or edges 22,24 of the blade 14. One or more securing means 41 may be provided along the length of the string 39 to secure the string 39 into position on the blade 14. In some embodiments, such securing means 41 comprises a holder.

In operation, the device 10 illustrated in FIGS. 30A and 30B is placed in the oropharyngeal cavity of a subject as described elsewhere herein. An ETT may be arranged to pass through one of the nostrils and advanced therein. When the distal part of the ETT reaches the nasopharynx, the ETT is arranged to pass through the hole 35 and over the ramp 76, thereby elevating the epiglottis elevating bar 120. Since the passage of the ETT through the nose may make the ETT more curved than usual and this can create a resistance in further advancement of the ETT, an additional ramp 127 may be joined to the inner surface 132 of the epiglottis elevating bar 120 to assist with directing the distal end of the ETT slightly backwards and towards the trachea. In these embodiments, the ramp 76 may be omitted to prevent excessive forward curvature of the distal end of the ETT. If the passage of the ETT is associated with resistance, the ETT may be removed and an introducer may be arranged to pass through a nostril and advanced in the trachea. The ETT may then be passed over the introducer and placed inside the trachea. The introducer may then be removed. After the ETT enters the trachea, its proximal end of the ETT may be fixed around the nose and may be connected to a ventilation means. The string 39 may be pulled out of the plurality of holes 37, thereby opening the cleft 36. The device 10 may then be removed from the mouth of the subject. The cleft 36 may facilitate the removal of the device 10 over the distal part of the ETT.

Throughout the foregoing description and the drawings, in which corresponding and like parts are identified by the same reference characters, specific details have been set forth in order to provide a more thorough understanding to persons skilled in the art. However, well known elements may not have been shown or described in detail or at all to avoid unnecessarily obscuring the disclosure.

As will be apparent to those skilled in the art in the light of the foregoing disclosure, many alterations and modifications are possible in the practice of this invention without departing from the scope thereof. Accordingly, the description and drawings are to be regarded in an illustrative, rather than a restrictive, sense.

The invention claimed is:

1. An airway device comprising:
    an elongated blade comprising:
        first and second longitudinal edges and proximal and distal lateral edges, each of the proximal and distal lateral edges connecting the first longitudinal edge to the second longitudinal edge at opposing sides thereof,
        a proximal region proximate to the proximal lateral edge, and a distal region proximate to the distal lateral edge,
    a pair of side components arranged laterally spaced-apart on the elongated blade, wherein each of the side components is arranged to project outwardly from a first face of the elongated blade at the distal region thereof;
    a distal plate region defined by a space separating the pair of side components, dimensioned for a device to pass therethrough towards a distal tip of the blade;
    an epiglottis elevating bar having a proximal lateral edge joined to the distal conduit, the epiglottis elevating bar being arranged to extend distally from the distal conduit towards the distal lateral edge of the elongated blade,
    a distal conduit extending laterally on the elongated blade, the distal conduit being arranged proximal or distal to proximal lateral sides of the side components along a longitudinal axis of the blade, the distal conduit defining a channel dimensioned to allow passage of the device; and
    and wherein the pair of side components each extends distally starting from a first point towards a second point on the first face of the elongated blade, and wherein the first and second points are positioned at the distal region of the elongated blade.

2. The airway device according to claim 1, wherein the pair of side components are arranged in mirror image symmetry with respect to a central longitudinal axis of the elongated blade.

3. The airway device according to claim 1, wherein the pair of side components each comprises a first longitudinal side projecting outwardly along a wall to an opposing second longitudinal side, and proximal and distal lateral sides each connecting the first longitudinal side to the second longitudinal side at opposite sides thereof, wherein the lateral cross-sectional area is greater at the proximal lateral side than at the distal lateral side.

4. The airway device according to claim 1, further comprising a ramp joined to the first face of the blade at the distal region thereof, wherein the ramp comprises a first ramp longitudinal side, an opposing second ramp longitudinal side, and proximal and distal ramp lateral sides each connecting the first ramp longitudinal side to the second ramp longitudinal side at opposing sides thereof, wherein the ramp comprises an upward sloping face and/or downward sloping face.

5. The airway device according to claim 4, further comprising one or more guiding plates projecting outwardly from an upward sloping face of the ramp, arranged to guide passage of the device thereon.

6. The airway device according to claim 1, wherein first and second longitudinal edges of the epiglottis elevating bar extend between the side components within the distal plate region.

7. The airway device according to claim 1, wherein a distal lateral edge, opposite to the proximal lateral edge, of the epiglottis elevating bar is arranged distal or proximal to a distal ramp lateral side of a ramp along the longitudinal axis of the blade.

8. The airway device according to claim 1, comprising attachment means projecting outwardly from an inner surface of the epiglottis elevating bar, adapted for securing the epiglottis elevating bar to an upward sloping face or a downward sloping face of a ramp and/or the first face of the blade.

9. The airway device according to claim 1, further comprising a pair of shelves each arranged to project inwardly toward a central axis of the blade from a wall of the respective side components, the pair of shelves being arranged in mirror image symmetry to one another with respect to a central longitudinal axis of the blade.

10. The airway device according to claim 1, further comprising a proximal conduit arranged at the proximal region of the blade, the proximal conduit defining a channel dimensioned for the device to pass therethrough.

11. The airway device according to claim 1, further comprising a rail joined on the first face or a second face of the blade, the rail defining a channel dimensioned to receive one or more second blades, wherein the one or more second blades is moveable within the channel along a longitudinal axis of the rail.

12. The airway device according to claim 11, wherein the rail comprises a first longitudinal rail arm, an opposing second longitudinal rail arm, and a lateral rail arm connecting the first and second longitudinal rail arms at distal ends of the longitudinal rail arms.

13. The airway device according to claim 11, further comprising one or more second blades, wherein the one or more second blades comprise a reinforcing blade with a thickness greater or less than a thickness of the blade.

14. The airway device according to claim 1, further comprising one or more tubes each extending proximally along a longitudinal axis of the blade, from a distal end of each of the one or more tubes to a proximal end thereof, wherein the distal end of each of the one or more tubes is arranged at or near the distal lateral edge of the blade.

15. The airway device according to claim 1, further comprising one or more cameras securable to the blade arranged to visualize laryngeal structures.

16. An airway device comprising:
an elongated blade comprising:
first and second longitudinal edges and proximal and distal lateral edges, each of the proximal and distal lateral edges connecting the first longitudinal edge to the second longitudinal edge at opposing sides thereof,
a proximal region proximate to the proximal lateral edge, and a distal region proximate to the distal lateral edge,
a pair of side components arranged laterally spaced-apart on the elongated blade, wherein each of the side components is arranged to project outwardly from a first face of the elongated blade at the distal region thereof;
a distal plate region defined by a space separating the pair of side components, dimensioned for a device to pass therethrough towards a distal tip of the blade;
a ramp joined to the first face of the blade at the distal region thereof, wherein the ramp comprises a first ramp longitudinal side, an opposing second ramp longitudinal side, and proximal and distal ramp lateral sides each connecting the first ramp longitudinal side to the second ramp longitudinal side at opposing sides thereof, the ramp being positioned between the pair of side components;
a distal conduit extending laterally on the elongated blade, the distal conduit being arranged proximal or distal to proximal lateral sides of the side components along a longitudinal axis of the blade, the distal conduit defining a channel dimensioned to allow passage of the device; and
an epiglottis elevating bar joined to the distal conduit at a proximal lateral edge of the epiglottis elevating bar, the epiglottis elevating bar being arranged to extend distally from the distal conduit, and above the ramp.

17. The airway device according to claim 16 further comprising a proximal conduit arranged at the proximal region of the blade, the proximal conduit defining a channel dimensioned for the device to pass therethrough.

18. The airway device according to claim 16, further comprising one or more tubes each extending proximally along a longitudinal axis of the blade, from a distal end of the tube to a proximal end thereof, wherein the distal end of the tube is arranged at or near the distal lateral edge of the blade.

19. The airway device according to claim 16, wherein the ramp comprises an upward sloping face and/or a downward sloping face.

20. An airway device comprising:
an elongated blade comprising:
first and second longitudinal edges and proximal and distal lateral edges, each of the proximal and distal lateral edges connecting the first longitudinal edge to the second longitudinal edge at opposing sides thereof,
a proximal region proximate to the proximal lateral edge, and a distal region proximate to the distal lateral edge,
a pair of side components arranged laterally spaced-apart on the elongated blade, wherein each of the side components is arranged to project outwardly from a first face of the elongated blade at the distal region thereof;
a distal plate region defined by a space separating the pair of side components, dimensioned for a device to pass therethrough towards a distal tip of the blade;
a ramp joined to the first face of the blade at the distal region thereof, wherein the ramp comprises a first ramp longitudinal side, an opposing second ramp longitudinal side, and proximal and distal ramp lateral sides each connecting the first ramp longitudinal side to the second ramp longitudinal side at opposing sides thereof, the ramp being positioned between the pair of side components;
one or more second blades; and
a rail joined on the elongated blade, the rail defining a channel dimensioned to receive the one or more second blades, wherein the one or more second blades is moveable within the channel along a longitudinal axis of the rail,
wherein the one or more second blades comprise a roll-down blade, and wherein the roll-down blade comprises an elongated body having first and second longitudinal sides and proximal and distal lateral sides, each the proximal and distal lateral sides connecting the first to the second longitudinal sides at opposite sides thereof,
and wherein the elongated blade defines an elongated slot between the first and second longitudinal edges of the elongated blade, the elongated slot being dimensioned for the roll-down blade to pass therethrough.

21. The airway device according to claim 20, further comprising a base guiding plate projecting outwardly from the first face of the blade, positioned distal to an elongated slot along the longitudinal axis of the blade.

22. The airway device according to claim 21, wherein a cleft is defined on a distal edge of the base guiding plate.

23. The airway device according to claim 21, further comprising a guide being secured within the rail at a distal end thereof, the guide being secured to the rail at a first end of the guide and to the base guiding plate at an opposing second end of the guide.

24. The airway device according to claim 20, wherein the side components each comprises a cleft defined on a respective wall thereof, the clefts arranged to face one another, in a mirror image symmetry with respect to a central longitudinal axis of blade.

25. The airway device according to claim 20 further comprising a proximal conduit arranged at the proximal region of the blade, the proximal conduit defining a channel dimensioned for the device to pass therethrough.

26. The airway device according to claim 20, further comprising one or more tubes each extending proximally along a longitudinal axis of the blade, from a distal end of each of the one or more tubes to a proximal end thereof, wherein the distal end of each of the one or more tubes is arranged at or near the distal lateral edge of the blade.

27. The airway device according to claim 20, wherein the ramp comprises an upward sloping face and/or a downward sloping face.

28. An airway device comprising:
an elongated blade comprising:
first and second longitudinal edges and proximal and distal lateral edges, each of the proximal and distal lateral edges connecting the first longitudinal edge to the second longitudinal edge at opposing sides thereof,
a proximal region proximate to the proximal lateral edge, and a distal region proximate to the distal lateral edge,
a pair of side components arranged laterally spaced-apart on the elongated blade, wherein each of the side components is arranged to project outwardly from a first face of the elongated blade at the distal region thereof;

a distal plate region defined by a space separating the pair of side components, dimensioned for a device to pass therethrough towards a distal tip of the blade;

a hole defined on the blade, a cleft extending from the hole to the distal tip of the blade, and a plurality of holes defined on the blade arranged at opposing sides of the cleft along a longitudinal length thereof; and a string arranged to pass through the plurality of holes from a distal end of the string to a proximal end thereof, wherein the string extends towards the proximal lateral edge of the blade, wherein the pair of side components each extends distally starting from a first point towards a second point on the first face of the elongated blade, and wherein the first and second points are positioned at the distal region of the elongated blade.

* * * * *